(12) United States Patent
Dong et al.

(10) Patent No.: US 12,158,416 B1
(45) Date of Patent: Dec. 3, 2024

(54) METHOD, DEVICE, AND SYSTEM FOR DETECTING SOIL ORGANIC MATTER

(71) Applicant: Research Center of Intelligent Equipment, Beijing Academy of Agriculture and Forestry Sciences, Beijing (CN)

(72) Inventors: Daming Dong, Beijing (CN); Hongwu Tian, Beijing (CN); Guiyan Yang, Beijing (CN); Shixiang Ma, Beijing (CN); Yueting Wang, Beijing (CN); Zhen Xing, Beijing (CN); Shuai Liu, Beijing (CN)

(73) Assignee: Research Center of Intelligent Equipment, Beijing Academy of Agriculture and Forestry Sciences, Beijing (CN)

( * ) Notice: Subject to any disclaimer, the term of this patent is extended or adjusted under 35 U.S.C. 154(b) by 0 days.

(21) Appl. No.: 18/788,971

(22) Filed: Jul. 30, 2024

(30) Foreign Application Priority Data

Dec. 25, 2023 (CN) .......................... 202311789117.8

(51) Int. Cl.
| | | |
|---|---|---|
| *G01N 21/31* | (2006.01) | |
| *G01N 21/35* | (2014.01) | |
| *G01N 21/3563* | (2014.01) | |
| *G01N 21/39* | (2006.01) | |
| *G01N 21/71* | (2006.01) | |
| *G01N 33/24* | (2006.01) | |

(52) U.S. Cl.
CPC ..... *G01N 21/3103* (2013.01); *G01N 21/3563* (2013.01); *G01N 21/39* (2013.01); *G01N 21/718* (2013.01); *G01N 2021/3572* (2013.01); *G01N 33/24* (2013.01)

(58) Field of Classification Search
CPC ........... G01N 21/3103; G01N 21/3563; G01N 21/39; G01N 21/718; G01N 33/24; G01N 2021/3572
See application file for complete search history.

(56) References Cited

FOREIGN PATENT DOCUMENTS

| CN | 104198445 A | 12/2014 | |
|---|---|---|---|
| CN | 111595806 A | 8/2020 | |
| CN | 115876544 A * | 3/2023 | ............... G01N 1/28 |

OTHER PUBLICATIONS

First Office Action issued Feb. 8, 2024 in Chinese Patent Application No. 202311789117.8, 16 pages.
Notification to Grant Patent Rights for Invention issued Mar. 14, 2024 in Chinese Patent Application No. 202311789117.8, 3 pages.

* cited by examiner

*Primary Examiner* — Jamil Ahmed
(74) *Attorney, Agent, or Firm* — Edell, Shapiro & Finnan, LLC

(57) ABSTRACT

Provided are a method, device, and system for detecting soil organic matter, which belong to the technical field of soil detection. The method includes: determining a total carbon content in a soil to be tested according to an atomic emission spectrum of a first pressed soil sample; determining an inorganic carbon content in the soil to be tested according to a molecular absorption spectrum of a second pressed soil sample; and finally determining an organic matter content in the soil to be tested according to the total carbon content and the inorganic carbon content.

10 Claims, 13 Drawing Sheets

```
┌─────────────────────────────────────────────────────┐
│ Irradiate the second pressed soil sample with a     │
│ broad-band infrared light source, and acquire the   │
│ molecular absorption spectrum of diffused light     │
│ reflected by the second pressed soil sample         │
└─────────────────────────────────────────────────────┘
                          │
                          ▼
┌─────────────────────────────────────────────────────┐
│ Acquire a background spectrum through a blank       │
│ sample, and calculate an absorbance curve of the    │
│ molecular absorption spectrum with the molecular    │
│ absorption spectrum and the background spectrum     │
└─────────────────────────────────────────────────────┘
                          │
                          ▼
┌─────────────────────────────────────────────────────┐
│ On the absorbance curve, acquire absorbance         │
│ corresponding to a characteristic frequency band of │
│ inorganic carbon components in the soil to be tested│
└─────────────────────────────────────────────────────┘
                          │
                          ▼
┌─────────────────────────────────────────────────────┐
│ Input the absorbance into a first inorganic carbon  │
│ content quantification model constructed in advance │
│ to obtain the inorganic carbon content output by    │
│ the first inorganic carbon content quantification   │
│ model                                               │
└─────────────────────────────────────────────────────┘
```

FIG. 9

METHOD, DEVICE, AND SYSTEM FOR DETECTING SOIL ORGANIC MATTER

CROSS REFERENCE TO RELATED APPLICATION

This patent application claims the benefit and priority of Chinese Patent Application No. 202311789117.8, filed with the China National Intellectual Property Administration on Dec. 25, 2023, the disclosure of which is incorporated by reference herein in its entirety as part of the present application.

TECHNICAL FIELD

The present disclosure relates to the technical field of soil detection, and in particular to a method, device, and system for detecting soil organic matter.

BACKGROUND

Soil organic matter refers to all carbon-containing organic substances in the soil, including animal and plant residues, microorganisms, and various organic substances resulting from decomposition and synthesis of microorganisms. Although a proportion of soil organic matter in the soil is small (1% to 20%), soil organic matter is of great significance. A soil organic matter content is an important index to measure a soil fertility level, and plays an important role in the soil fertility, environmental protection, and sustainable agricultural development.

Currently, a method for determining a soil organic matter content is generally as follows: a surface of a soil sample is irradiated with a light source of a visible-to-near-infrared waveband, the band selection and model construction are conducted based on statistical laws, reflected light of different wavelengths on the surface of the soil sample are detected to establish a multi-parameter soil organic matter calculation model, and the established multi-parameter soil organic matter calculation model is used in the actual detection of a soil organic matter content.

However, since organic matters do not have a distinct characteristic in a spectrum, the reflected light of different wavelengths resulting from the irradiation of the surface of the soil sample with the light source of the visible-to-near-infrared waveband can only reflect a soil organic matter content indirectly. In addition, due to the severe impacts of soil matrix effects, including impacts of factors such as a soil type, a soil color, a soil particle size, and a soil moisture content, different soil types, different spectrum acquisition devices, and different physical and chemical properties of a soil sample will lead to completely different results, such that it is difficult to obtain a soil organic matter inversion model with strong universality and a resulting model has a poor migration effect.

Therefore, during the early modeling of the soil organic matter calculation model, it is necessary to collect and treat a large number of soil samples to ensure that modeling samples cover all possible sample types as much as possible, resulting in high labor and time costs.

SUMMARY

The present disclosure provides a method, device, and system for detecting soil organic matter to solve the defect that the soil organic matter detection model in the prior art has a poor migration effect and high modeling labor and time costs.

In a first aspect, the present disclosure provides a method for detecting soil organic matter, including:
  determining a total carbon content in a soil to be tested according to an atomic emission spectrum of a first pressed soil sample, where the first pressed soil sample is a sample of the soil to be tested;
  determining an inorganic carbon content in the soil to be tested according to a molecular absorption spectrum of a second pressed soil sample, where the second pressed soil sample is prepared by mixing the sample of the soil to be tested with an infrared light transmitting material in a preset ratio;
  determining an organic carbon content in the soil to be tested according to a difference between the total carbon content and the inorganic carbon content; and
  determining an organic matter content in the soil to be tested according to the organic carbon content.

According to the method for detecting soil organic matter provided by the present disclosure, the determining a total carbon content in a soil to be tested according to an atomic emission spectrum of a first pressed soil sample specifically includes:
  ablating the first pressed soil sample with pulsed laser to excite soil particles in the first pressed soil sample into a high temperature plasma with energy level transition;
  acquiring the atomic emission spectrum generated during a cooling and de-excitation process of the high temperature plasma with energy level transition;
  extracting an intensity of a characteristic spectral line of carbon from the atomic emission spectrum; and
  inputting the intensity of the characteristic spectral line of the carbon into a total carbon content quantification model constructed in advance to obtain the total carbon content output by the total carbon content quantification model.

According to the method for detecting soil organic matter provided by the present disclosure, during a process of ablating the first pressed soil sample with the pulsed laser, an inert gas is purged around an ablation point.

According to the method for detecting soil organic matter provided by the present disclosure, the determining an inorganic carbon content in the soil to be tested according to a molecular absorption spectrum of a second pressed soil sample specifically includes:
  irradiating the second pressed soil sample with a broadband infrared light source, and acquiring the molecular absorption spectrum of diffused light reflected by the second pressed soil sample;
  acquiring a background spectrum through a blank sample, and calculating an absorbance curve of the molecular absorption spectrum with the molecular absorption spectrum and the background spectrum;
  on the absorbance curve, acquiring absorbance corresponding to a characteristic frequency band of inorganic carbon components in the soil to be tested; and
  inputting the absorbance into a first inorganic carbon content quantification model constructed in advance to obtain the inorganic carbon content output by the first inorganic carbon content quantification model.

According to the method for detecting soil organic matter provided by the present disclosure, the determining an inorganic carbon content in the soil to be tested according to a molecular absorption spectrum of a second pressed soil sample specifically includes:

determining a characteristic waveband corresponding to inorganic carbon components in the soil to be tested;

controlling a tunable laser to generate a continuous narrow-band infrared laser capable of covering the characteristic waveband to irradiate the second pressed soil sample;

acquiring the molecular absorption spectrum of a laser transmitted through the second pressed soil sample;

determining an absorption spectral intensity within the characteristic waveband in the molecular absorption spectrum; and inputting the absorption spectral intensity into a second inorganic carbon content quantification model constructed in advance to obtain the inorganic carbon content output by the second inorganic carbon content quantification model.

According to the method for detecting soil organic matter provided by the present disclosure, the characteristic waveband is in a range of 1,300 cm$^{-1}$ to 1,600 cm$^{-1}$.

According to the method for detecting soil organic matter provided by the present disclosure, the determining an organic matter content in the soil to be tested according to the organic carbon content includes:

inputting the organic carbon content into an organic matter content quantification model constructed in advance to obtain the organic matter content output by the organic matter content quantification model.

In a second aspect, the present disclosure also provides a device for detecting soil organic matter, including:

a total carbon content determination unit configured to determine a total carbon content in a soil to be tested according to an atomic emission spectrum of a first pressed soil sample, where the first pressed soil sample is a sample of the soil to be tested;

an inorganic carbon content determination unit configured to determine an inorganic carbon content in the soil to be tested according to a molecular absorption spectrum of a second pressed soil sample, where the second pressed soil sample is prepared by mixing the sample of the soil to be tested with an infrared light transmitting material in a preset ratio;

an organic carbon content determination unit configured to determine an organic carbon content in the soil to be tested according to a difference between the total carbon content and the inorganic carbon content; and an organic matter content determination unit configured to determine an organic matter content in the soil to be tested according to the organic carbon content.

In a third aspect, the present disclosure also provides a system for detecting soil organic matter, at least including the device for detecting soil organic matter and further including:

a pulsed laser output device configured to output pulsed laser;

a focusing lens configured to focus the pulsed laser to ablate the first pressed soil sample;

a protective gas-purging device configured to purge an inert gas around an ablation point of the first pressed soil sample;

a spectrum acquisition device arranged opposite to the pulsed laser output device and configured to acquire the atomic emission spectrum generated after soil particles in the first pressed soil sample are excited into a high temperature plasma with energy level transition;

a sample-moving platform configured to carry the first pressed soil sample and adjust an ablation point of the pulsed laser by controlling the first pressed soil sample to move in different directions;

a broad-band infrared light source configured to output broad-band infrared light to the second pressed soil sample; and a first infrared detection spectrometer arranged opposite to the broad-band infrared light source and configured to acquire the molecular absorption spectrum of diffused light reflected by the second pressed soil sample.

The system for detecting soil organic matter provided by the present disclosure further includes:

a tunable laser provided with a laser controller and configured to generate a continuous narrow-band infrared laser capable of covering a characteristic waveband corresponding to inorganic carbon components; and a second infrared detection spectrometer arranged opposite to the tunable laser and configured to acquire the molecular absorption spectrum of a transmitted laser transmitted through the second pressed soil sample.

According to the system for detecting soil organic matter provided by the present disclosure, a substrate of the second pressed soil sample is a high-reflectivity substrate.

In the method, device, and system for detecting soil organic matter provided by the present disclosure, based on the distinct characteristics of carbon and inorganic carbon in an atomic emission spectrum and a molecular absorption spectrum, the atomic emission spectroscopy technology and the molecular absorption spectroscopy technology are used in combination. Different light sources are used to ablate or irradiate different pressed soil samples to obtain total carbon content and inorganic carbon content, and an organic matter content is calculated. For soil samples in different regions, there is no need of a large number of samples to construct an organic matter content inversion model, which improves the universality and transplantability of the detection method and reduces the time and labor costs of soil organic matter detection.

BRIEF DESCRIPTION OF THE DRAWINGS

To describe the technical solutions in the present disclosure or in the prior art clearly, the accompanying drawings required for describing the embodiments or the prior art are briefly described below. Apparently, the accompanying drawings in the following description show some embodiments of the present disclosure, and a person of ordinary skill in the art may still derive other accompanying drawings from these accompanying drawings without creative efforts.

FIG. 9 is a schematic flow chart of the method for detecting an inorganic carbon content in a soil based on diffuse reflection provided by the present disclosure;

REFERENCE NUMERALS

Figure 1:
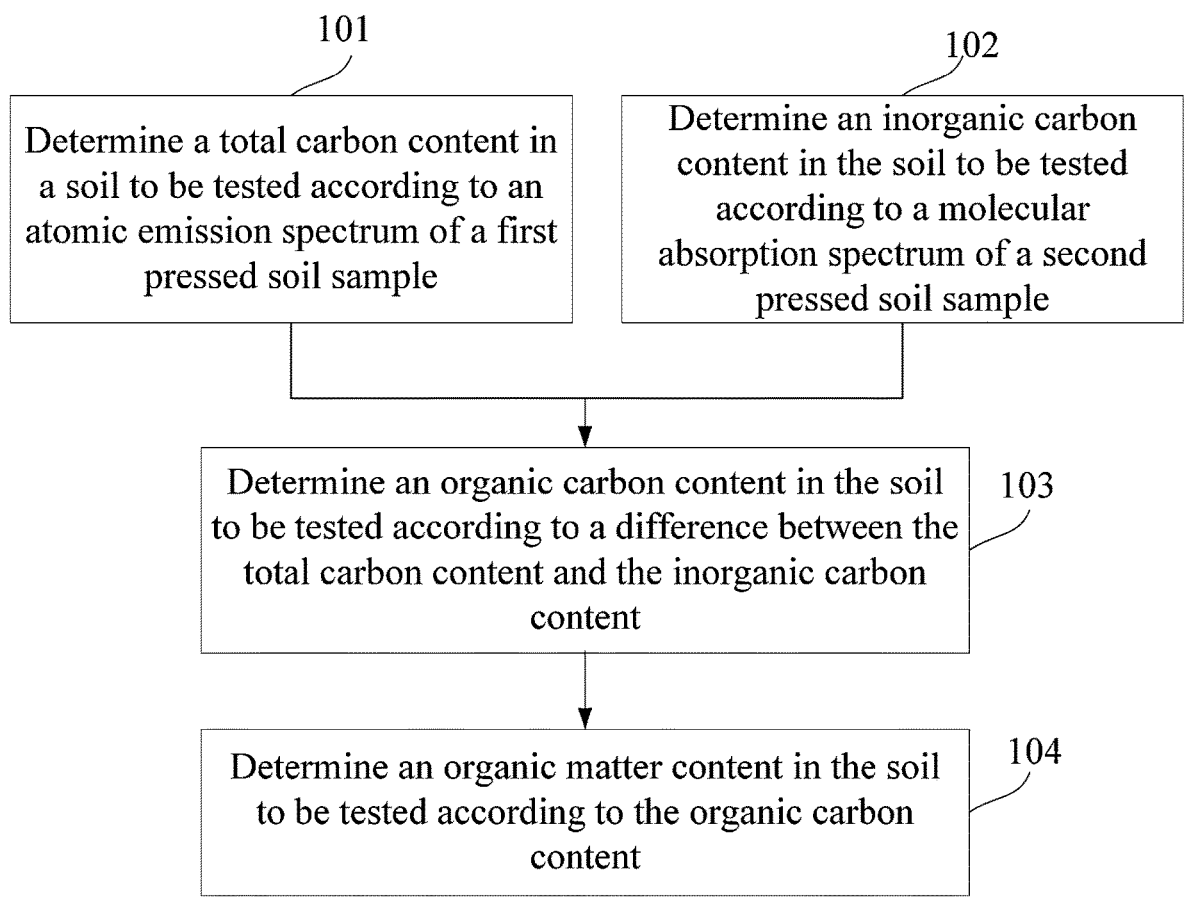
FIG. 1 is a schematic flow chart of the method for detecting soil organic matter provided by the present disclosure.

1: soil sample; 2: gasket; 3: base; 4: upper pressure head; 5: pressure device; 6: demolding sleeve; 11: pulsed laser output device; 12: broad-band infrared light source; 13: tunable laser; 20: protective gas-purging device; 31: spectrum acquisition device; 32: first infrared detection spectrometer; 33: second infrared detection spectrometer; 40: sample-moving platform; 51: first pressed soil sample; 52: second pressed soil sample; 60: sample substrate; 61: ordinary substrate; 62: high-reflectivity substrate; 70: laser controller; 901: total carbon content determination unit; 902: inorganic carbon content determination unit; 903: organic carbon content determination unit; and 904: organic matter content determination unit.

DETAILED DESCRIPTION OF THE EMBODIMENTS

To make the objectives, technical solutions, and advantages of the present disclosure clear, the technical solutions in the present disclosure are clearly and completely described below with reference to the accompanying drawings in the present disclosure. Apparently, the described embodiments are some rather than all of the embodiments of the present disclosure. All other embodiments obtained by those of ordinary skill in the art based on the embodiments of the present disclosure without creative efforts should fall within the protection scope of the present disclosure.

It should be noted that, in the description of the embodiments of the present disclosure, terms "including", "comprising", or any other variants thereof are intended to cover non-exclusive inclusion, such that a process, method, article, or device including a series of elements includes not only those elements but also other elements not explicitly listed, or elements inherent to such a process, method, article, or device. Without additional restrictions, the elements defined by the sentence "including a . . . " do not exclude the existence of other identical elements in a process, method, article, or device including the elements. An orientation or position relationship indicated by a term such as "upper" or "lower" is based on the orientation or position relationship shown in the accompanying drawings. These terms are just used to facilitate and simplify the description of the present disclosure, but not to indicate or imply that the mentioned device or components must have a specific orientation and must be constructed and operated in a specific orientation. Therefore, these terms cannot be understood as a limitation to the present disclosure. Unless otherwise clearly specified and limited, terms such as "connected to" should be understood in a broad sense. For example, a connection may be a fixed connection, a detachable connection, or an integrated connection, may be a mechanical connection or an electrical connection, may be a direct connection or an indirect connection via an intermediate medium, or may be intercommunication between two components. Those of ordinary skill in the art may understand specific meanings of the above terms in the present disclosure based on a specific situation.

The terms such as "first" and "second" in the present disclosure are intended to distinguish between similar objects, rather than to describe a specific order or sequence. It should be understood that data used in this way may be interchanged under appropriate circumstances such that the embodiments of the present disclosure can be implemented in an order other than those illustrated or described herein, the objects distinguished by "first", "second", or the like are usually of one type, and the number of objects is not limited. For example, one or more first objects may be provided. In addition, "and/or" means at least one of associated objects, and the character "/" generally indicates an "or" relationship between associated objects.

A standard method for determining soil organic matter is generally laboratory chemical analysis, where an organic carbon content is determined by a dichromate thermal oxidation method and then multiplied by a constant to obtain a soil organic matter content. However, the dichromate thermal oxidation method requires professional operations, a complicated process, and a lot of manpower and reagent consumables, produces a waste including highly-toxic chromium, and cannot guarantee the timeliness of detection.

The current methods for determining a soil organic matter content include a method for detecting soil organic matter based on diffuse reflectance spectrometry in a visible-to-near-infrared waveband, which is specifically as follows: a surface of a soil sample is irradiated with a light source of a visible-to-near-infrared waveband (such as a light-emitting diode (LED) light source and a photosensor), the band selection and model construction are conducted based on statistical laws, reflected light of different wavelengths on the surface of the soil sample are detected to establish a multi-parameter soil organic matter calculation model, and the established multi-parameter soil organic matter calculation model is used in the actual detection of a soil organic matter content.

Compared with the dichromate thermal oxidation method, the method for detecting soil organic matter based on diffuse reflectance spectrometry can allow the detection outside a laboratory and has the advantages of environmental friendliness and no chemical pollution.

However, since organic matters do not have a distinct characteristic in a spectrum, the reflected light of different wavelengths resulting from the irradiation of the surface of the soil sample with the light source of the visible-to-near-infrared waveband can only reflect a soil organic matter content indirectly. In addition, due to the severe impacts of soil matrix effects, including impacts of factors such as a soil type, a soil color, a soil particle size, and a soil moisture content, different soil types, different spectrum acquisition devices, and different physical and chemical properties of a soil sample will lead to completely different results, such that it is difficult to obtain a soil organic matter inversion model with strong universality, and a resulting model is merely suitable for soil samples in a same region and has a poor migration effect.

Therefore, during the early modeling of a soil organic matter calculation model, it is necessary to collect and treat a large number of soil samples to ensure that modeling samples cover all possible sample types as much as possible, which results in high labor and time costs and restricts the promotion and application of a detection device.

In view of this, the present disclosure provides a novel method for detecting soil organic matter, which is specifically illustrated below with reference to the descriptions of FIG. 1 to FIG. 17.

In view of the defects in the prior art, the present disclosure provides a method for rapidly detecting a soil organic matter content using spectroscopic techniques in combination. In the method, mainly based on soil components with distinct spectral characteristics, the soil components are subjected to quantitative analysis through a combination of an emission spectrum and an absorption spectrum, which solves the shortcoming that the inversion of a soil organic matter content relies on the modeling with a large number of samples and the chemometrics due to unclear spectral characteristics of organic matters in visible/near-infrared spectroscopy, and improves the universality and transplantability of the detection method. In addition, the method of the present disclosure does not require complicated treatments and chemical reactions for soil samples, does not require the participation of harmful chemical reagents, and does not cause secondary pollution. Therefore, the method of the present disclosure is an eco-friendly and efficient method for detecting soil organic matter.

FIG. 1 is a schematic flow chart of the method for detecting soil organic matter provided by the present disclosure. As shown in FIG. 1, the method includes, but is not limited to, the following steps:

Step 101: A total carbon content in a soil to be tested is determined according to an atomic emission spectrum of a first pressed soil sample. The first pressed soil sample is a sample of the soil to be tested.

Atomic emission spectrometry is an analytical method where a spectrum generated by radiations emitted by excited atoms is compared with a standard spectrum to identify what substances are included in a material and determine contents of the substances.

Specifically, a high-energy laser can excite different atoms into a high temperature plasma with energy level transition, and during a cooling and de-excitation process of the high temperature plasma with energy level transition, radiations are emitted to produce an atomic emission spectrum. Atoms of different elements correspond to atomic emission spectra with different characteristic wavelengths, that is, merely spectral lines of some wavelengths can be generated. After various atoms in the first pressed soil sample are excited, whether the soil includes carbon can be analyzed according to whether there is a characteristic spectral line of carbon in the atomic emission spectrum, and a content of carbon can be determined according to an intensity of the characteristic spectral line of carbon in the atomic emission spectrum.

Based on the above principle, the present disclosure adopts atomic emission spectrometry to detect a total content of carbon in the soil to be tested.

A sampling site and a sampling depth for the soil to be tested can be determined according to factors such as a research objective and soil characteristics. After the sampling site and the sampling depth for the soil to be tested are determined, an original soil sample is collected with a soil collection tool, sieved with a sieve to remove obvious impurities such as gravel, grass roots, and animal and plant residues in the soil sample, and then naturally air-dried to remove moisture to obtain a soil sample with relatively uniform physical properties such as a particle size.

The first pressed soil sample for detecting the total carbon content in the soil to be tested is prepared by a direct sheeting method as follows: a specified mass of a soil sample produced after sieving and air-drying is taken and directly sheeted by a sheeting tool with a fixed pressure for a fixed time to obtain the first pressed soil sample with a specified shape and a specified area.

The soil collection tool mentioned here can be a special geotome, a sample scoop, a probe, a needle sampler, or the like and the sheeting tool can be a manual sheeting machine, an automatic sheeting machine, a hydraulic sheeting machine, a rotary sheeting machine, or the like, but the present disclosure is not limited thereto.

For example, 1 g of a soil produced after sieving and air-drying is taken with an electronic balance as a soil sample, and the soil sample is sheeted by the sheeting tool with a fixed pressure for a fixed time to prepare the first pressed soil sample that has a diameter of 10 mm and is a thin cylindrical sheet.

Figure 2:
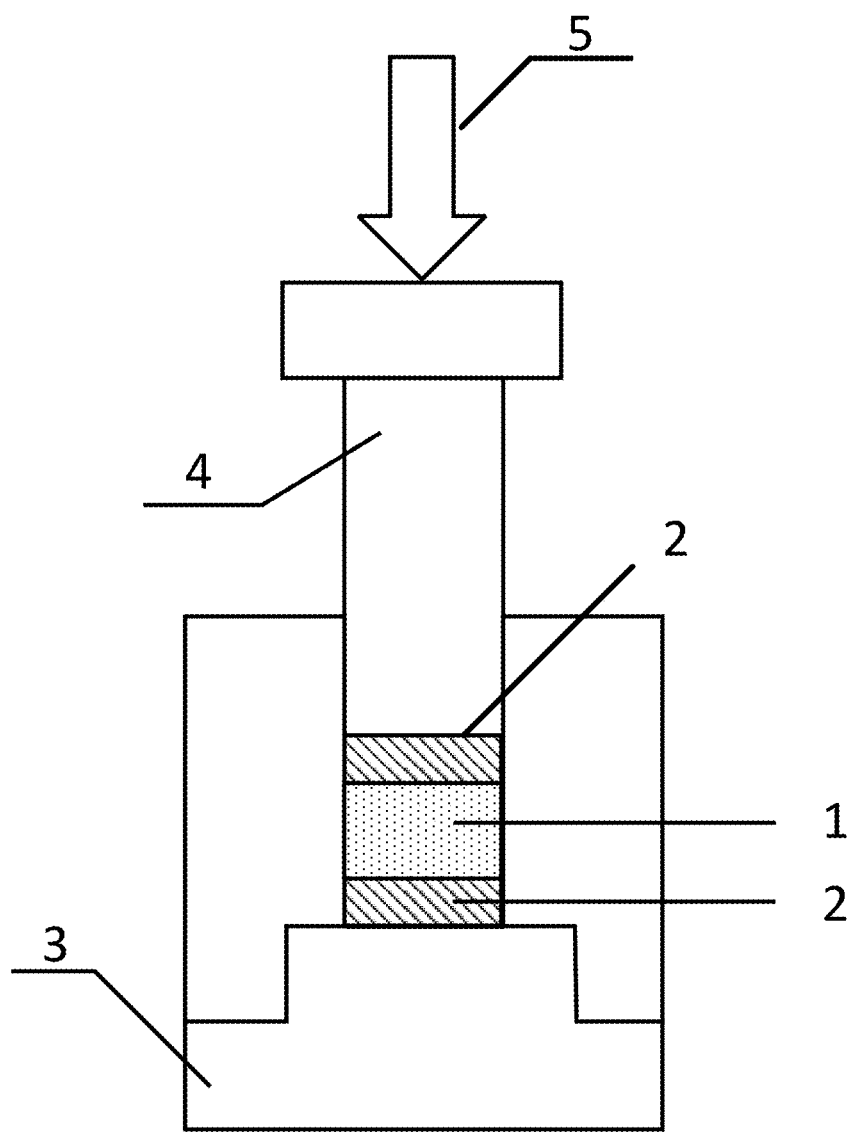
FIG. 2 is a schematic diagram of the preparation of a first pressed soil sample provided by the present disclosure.
Figure 3:
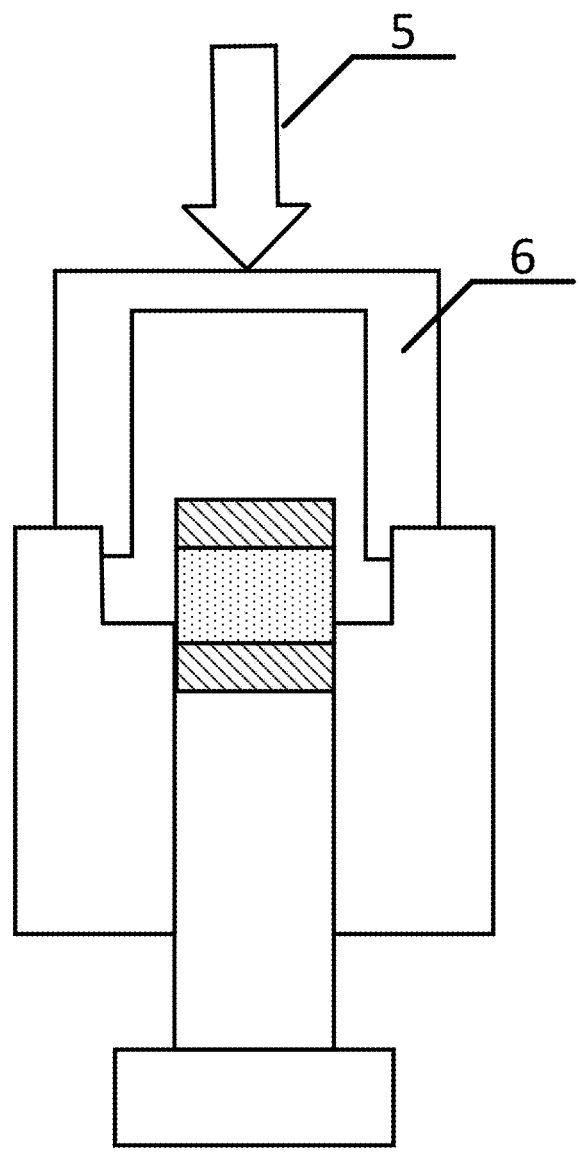
FIG. 3 is a schematic diagram of the demolding of a first pressed soil sample provided by the present disclosure.

FIG. 2 is a schematic structural diagram of the preparation of the pressed soil sample provided by the present disclosure and FIG. 3 is a schematic structural diagram of the demolding of the pressed soil sample provided by the present disclosure. As shown in FIG. 2 and FIG. 3, in an optional embodiment, the sheeting tool used for preparing the pressed soil sample mainly includes gaskets 2, a base 3, an upper pressure head 4, a pressure device 5, and a demolding sleeve 6, and the soil sample 1 is arranged between two gaskets 2.

During an actual preparation process, a fixed pressure is set for the pressure device 5 to apply the fixed pressure to the upper pressure head 4 within a preset period of time, and the fixed pressure acts on the gaskets 2 in contact with the upper pressure head 4 to squeeze the soil sample 1 downwards until the pressed soil sample is produced.

Then, the pressed soil sample needs to be demolded, specifically including: The overall structure is turned over and the base 3 is replaced by the demolding sleeve 6. A pressure is further applied to the upper pressure head 4 through the pressure device 5. Under an action of this pressure, the pressed soil sample moves inside the demolding sleeve 6 until completely leaving a mold cavity to obtain a released pressed soil sample.

The first pressed soil sample can be prepared in the above way. It should be noted that the soil sample used for preparing the first pressed soil sample is completely composed of the soil to be tested.

A second pressed soil sample can also be prepared in the same way as the first pressed soil sample, except that a soil sample used for preparing the second pressed soil sample is a mixed sample of a sample collected from the soil to be tested and an infrared light transmitting material in a preset ratio.

Step 102: An inorganic carbon content in the soil to be tested is determined according to a molecular absorption spectrum of a second pressed soil sample.

Inorganic carbon in soil mainly exists in the form of carbonates. Most soils actually have a very low content of inorganic carbon, which can be basically ignored. A small number of soils, such as calcareous soils, include a specified amount of inorganic carbon, which mainly exists in the form of carbonates. Therefore, in this embodiment, a content of carbonates in the soil is approximately regarded as a content of inorganic carbon in the soil, so as to fully consider the accuracy of the result.

Carbonate molecules have a significant infrared spectroscopy activity, and an inorganic carbonate content in the soil can be detected through a molecular absorption spectrum of carbonate molecules. Specifically, when a soil sample is irradiated with infrared light, molecules in a soil vibrate and rotate to produce infrared absorption signals of different wavelengths. Carbonate ions in carbonate components have specific vibration modes and exhibit characteristic infrared absorption peaks (also known as spectral bands) that can be used to identify and analyze a carbonate component content in a soil sample.

When the second pressed soil sample for detecting the inorganic carbon content in the soil to be tested is prepared, a mixed sheeting method can be adopted. That is, after a soil sample produced after sieving and air-drying is mixed with an infrared light transmitting material in a preset ratio to obtain a mixed soil sample, the mixed soil sample is sheeted by the sheeting tool with a fixed pressure for a fixed time to obtain the second pressed soil sample with a specified shape and a specified area. Here, the soil sample and the infrared light transmitting material can be mixed by an electric mixer.

The infrared light transmitting material is a material with high infrared transmittance. For example, the infrared light transmitting material can be potassium bromide (KBr), zinc selenide (ZnSe), cadmium sulfide (CdS), calcium fluoride ($CaF_2$), or the like, but the present disclosure is not limited thereto.

The preset ratio of the soil sample to the infrared light transmitting material can be comprehensively determined according to factors such as a research objective, physical and chemical characteristics of the soil, and a type of the infrared light transmitting material.

For example, when KBr is adopted as the infrared light transmitting material, the preset ratio of the soil sample to the KBr can be any ratio in the range of 1:50 to 1:100.

For example, 1 g of a soil produced after sieving and air-drying is taken with an electronic balance as a soil sample, and the soil sample is sheeted by the sheeting tool with a fixed pressure for a fixed time to prepare the second pressed soil sample that has a diameter of 10 mm and is a thin cylindrical sheet.

For example, a ratio of the soil to the KBr is set to 1:50. 0.02 g of a soil sample produced after sieving and air-drying is taken with an electronic balance, 1 g of a KBr powder is taken, and the soil sample and the KBr powder are mixed and sheeted by the sheeting tool with a fixed pressure for a fixed time to finally prepare the second pressed soil sample that has a diameter of 10 mm and is a thin cylindrical sheet.

In another embodiment, a proportional model between the total inorganic carbon content and the carbonate content in the soil is constructed in advance. When the inorganic carbon content in the soil to be tested is determined according to the molecular absorption spectrum of the second pressed soil sample, a proportional difference between a carbonate content and a total inorganic carbon content in the soil to be tested is considered and converted, so as to determine the inorganic carbon content in the soil to be tested accurately.

Step 103: An organic carbon content in the soil to be tested is determined according to a difference between the total carbon content and the inorganic carbon content.

Soil organic matter refers to all carbon-containing organic substances in a soil, and carbon in a soil refers to a sum of organic carbon and inorganic carbon.

Currently, the chemical oxidation and thermal oxidation-based determination of a total carbon content and an organic carbon content in a soil is usually conducted by a dry combustion method (which is generally conducted at a high temperature of higher than 1,000° C.) or a dichromate redox colorimetric method, but this method has disadvantages such as long time, low determination efficiency, large chemical reagent consumption during a redox reaction, and secondary pollution risk caused by the heavy metal of chromium (Cr).

In the present disclosure, based on the principle that a total carbon content in a soil is equal to a sum of an organic carbon content and an inorganic carbon content, the total carbon content in the soil to be tested is detected according to the atomic emission spectrum of carbon in the first pressed soil sample, the inorganic carbon content in the soil to be tested is detected according to the molecular absorption spectrum of inorganic carbon molecules in the second pressed soil sample, and the difference between the total carbon content and the inorganic carbon content is determined as the organic carbon content in the soil to be tested, which has advantages such as a simple sample treatment, a high detection speed, no participation of complicated chemical reagents, and effective avoidance of environmental pollution caused by experimental wastes.

Step 104: An organic matter content in the soil to be tested is determined according to the organic carbon content.

A carbon content in soil organic matter refers to soil organic carbon, and there is a conversion relation between soil organic matter and soil organic carbon. That is, a ratio of soil organic matter to soil organic carbon is a carbon content ratio in the soil to be tested.

For example, a "Van Bemmelen factor" is used to determine the conversion relation between soil organic matter and soil organic carbon. That is, assuming that a carbon content ratio of the soil to be tested is 58%, the organic matter content in the soil to be tested can be calculated according to the following calculation formula:

$$TOM=((C_{Total}-C_{Inorganic})\times 1.724,$$

where TOM represents the organic matter content in the soil to be tested, $C_{Total}$ represents the total carbon content in the soil to be tested, $C_{Inorganic}$ represents the organic carbon content in the soil to be tested, and 1.724 is an approximate value of a reciprocal of the carbon content ratio of the soil to be tested.

Compared with the near-infrared spectroscopy-based detection method, the spectral characteristic waveband selected by the present disclosure is clear and has a small bandwidth, which avoids the characteristic waveband screening with chemometrics and the influence of different soil matrix effects on the migration and transitivity of a model.

In addition, the detection method designed by the present disclosure has a small sample consumption, a small reaction cross-section, and a small characteristic spectral bandwidth, and can effectively inhibit the influence of a soil texture, a soil type, and a soil matrix effect on an accuracy of a detection result.

In the method for detecting soil organic matter provided by the present disclosure, based on the distinct characteristics of carbon and inorganic carbon in an atomic emission spectrum and a molecular absorption spectrum, the atomic emission spectroscopy technology and the molecular absorption spectroscopy technology are used in combination. Different light sources are used to ablate or irradiate different pressed soil samples to obtain a total carbon content and an inorganic carbon content in a soil, and an organic matter content is calculated. For soils in different regions, there is no need of a large number of samples to construct an organic matter content inversion model, which improves the universality and transplantability of the detection method and reduces the time and labor costs of soil organic matter detection.

Figure 4:
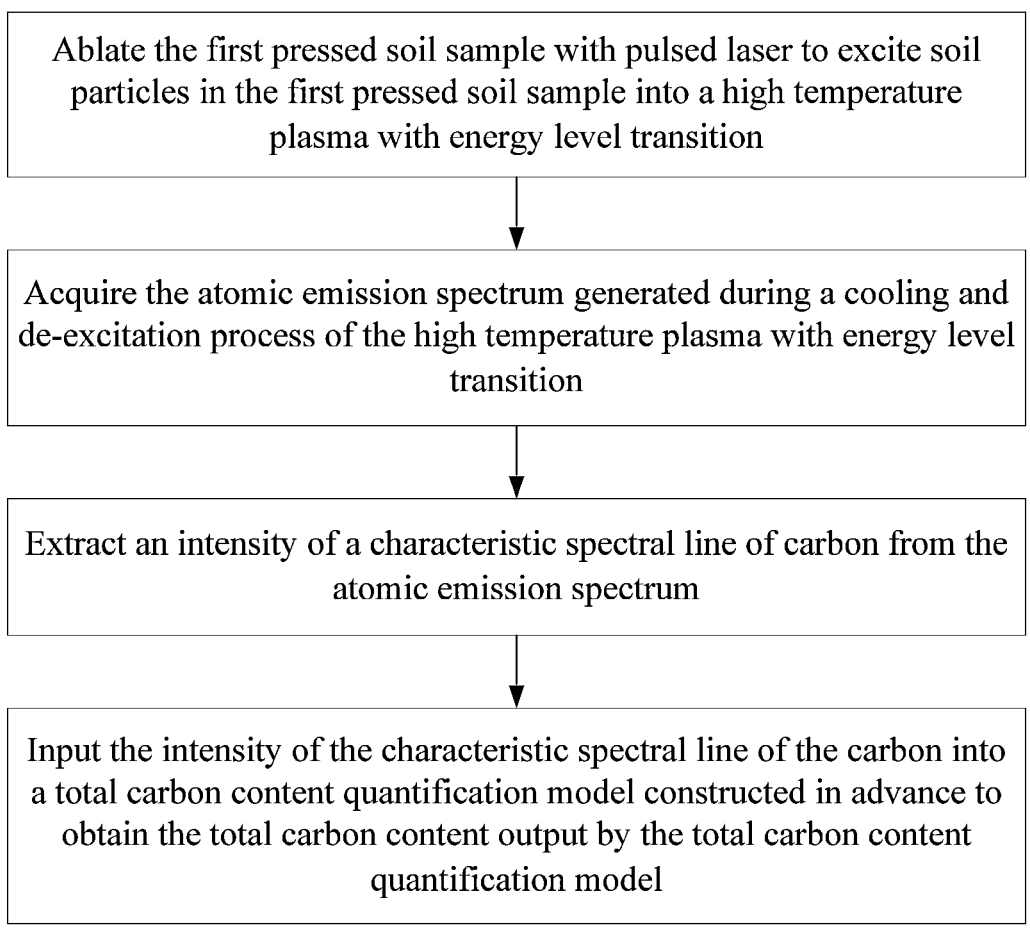
FIG. 4 is a schematic flow chart of the method for detecting a total carbon content in a soil provided by the present disclosure.

FIG. 4 is a schematic flow chart of the method for detecting a total carbon content in a soil provided by the present disclosure. As an optional embodiment, as shown in FIG. 4, the method of the present disclosure includes, but is not limited to, the following steps:

The determining the total carbon content in the soil to be tested according to the atomic emission spectrum of the first pressed soil sample specifically includes:

The first pressed soil sample is ablated with pulsed laser to excite soil particles in the first pressed soil sample into a high temperature plasma with energy level transition.

The atomic emission spectrum generated during a cooling and de-excitation process of the high temperature plasma with energy level transition is acquired.

An intensity of a characteristic spectral line of carbon is extracted from the atomic emission spectrum.

The intensity of the characteristic spectral line of the carbon is input into a total carbon content quantification model constructed in advance to obtain the total carbon content output by the total carbon content quantification model.

Specifically, a pulsed laser output device is provided with a fixed output energy and a fixed focusing area to output pulsed laser of a specified wavelength and energy, and the pulsed laser is focused on a surface of the first pressed soil sample through a focusing lens to ablate the first pressed soil sample, such that the soil particles in the first pressed soil sample are excited into the high temperature plasma with energy level transition.

The atomic emission spectrum generated during the cooling and de-excitation process of the high temperature plasma with energy level transition is acquired by a spectrum acquisition device and then output and displayed on an interface of the device, and the atomic emission spectrum includes characteristic spectral lines of different elements. Then, the intensity of the characteristic spectral line of carbon in the first pressed soil sample is extracted and input into the total carbon content quantification model constructed in advance to obtain the total carbon content in the soil to be tested that is output by the total carbon content quantification model.

Figure 5:
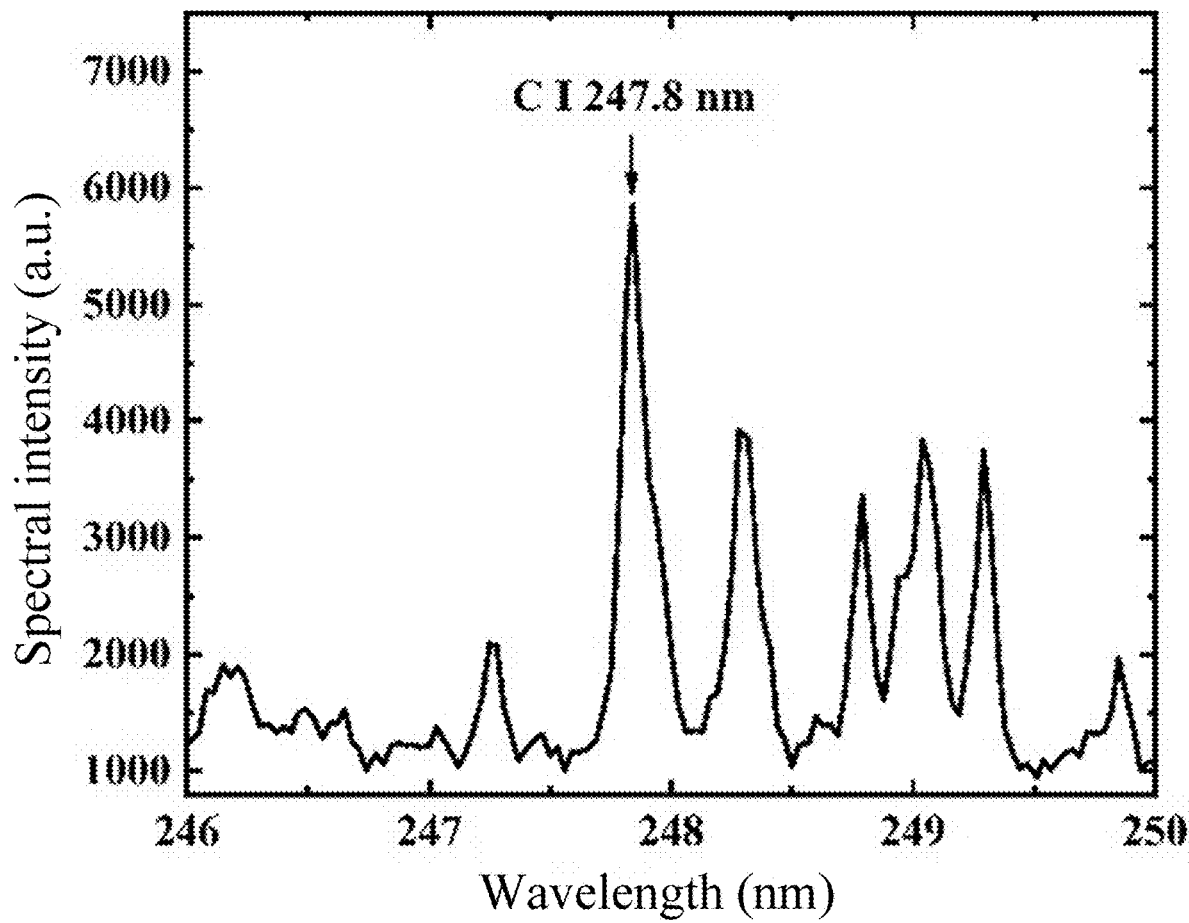
FIG. 5 is an example of the atomic emission spectrum provided by the present disclosure.

FIG. 5 is an example of the atomic emission spectrum provided by the present disclosure. With FIG. 5 as an example, pulsed laser is emitted by the pulsed laser output device with an emission wavelength of 1,064 nm to ablate the first pressed soil sample to excite soil particles in the first pressed soil sample into a high temperature plasma with energy level transition, and an atomic emission spectrum generated during a cooling and de-excitation process of the high temperature plasma with energy level transition is acquired by the spectrum acquisition device to obtain the atomic emission spectrum shown in FIG. 5. A characteristic spectral line at 247.8 nm on the atomic emission spectrum is a characteristic spectral line of carbon.

The total carbon content quantification model is a description of a relationship between the intensity of the characteristic spectral line of carbon and the total carbon content.

When the total carbon content quantification model is constructed in advance, a plurality of soil samples with known total carbon contents presenting a specified gradient are collected, atomic emission spectra of the plurality of soil samples are acquired by the atomic emission spectrometry, and intensities of characteristic spectral lines of carbon are extracted. An intensity of a characteristic spectral line of carbon in each sample is correlated with a corresponding carbon content, and these data points are fit by a regression method such as linear regression or polynomial regression to establish the total carbon content quantification model.

Figure 6:
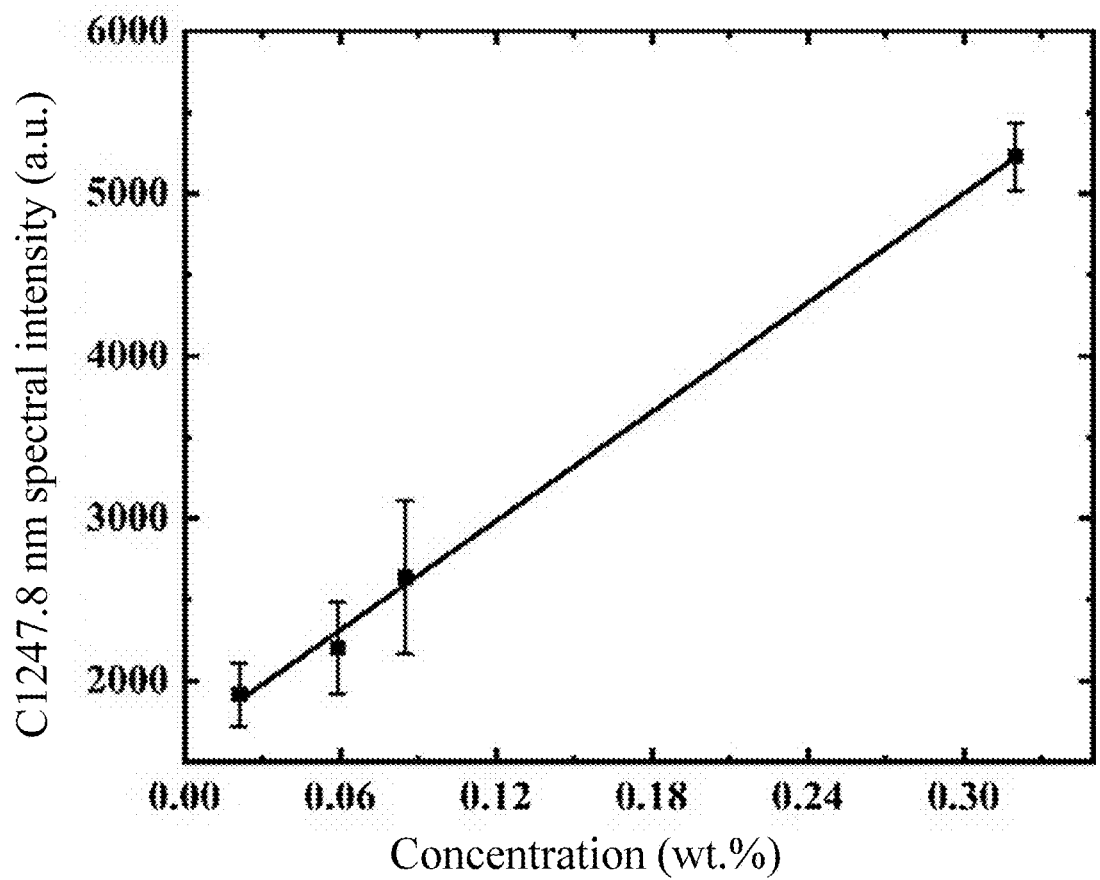
FIG. 6 is an example of the total carbon content quantification model provided by the present disclosure.

FIG. 6 is an example of the total carbon content quantification model provided by the present disclosure. With FIG. 6 as an example, a plurality of soil samples with known total carbon contents presenting a specified gradient are collected, atomic emission spectra of the plurality of soil samples are acquired by the atomic emission spectrometry, an intensity of a characteristic spectral line at 247.8 nm on each atomic emission spectrum is taken as an intensity of a characteristic spectral line of carbon, and an intensity of a characteristic spectral line of carbon in each sample is correlated with a corresponding carbon content to finally determine the total carbon content quantification model shown in FIG. 6.

In an embodiment, a measurement system for an atomic emission spectrum specifically includes, but is not limited to, a pulsed laser output device, a focusing lens, an acquisition optical fiber, a spectrometer, or the like.

In an embodiment, when an atomic emission spectrum is acquired by the spectrum acquisition device, an excitation time of a laser, a purge time of a purge gas, an acquisition time of a spectrum signal, and a trigger sequence thereof are also recorded.

In another embodiment, after a surface of the first pressed soil sample is ablated with the pulsed laser, the acquisition of the atomic emission spectrum generated during the cooling and de-excitation process of the high temperature plasma with energy level transition by the spectrum acquisition device is delayed by a specified time, such that an atomic emission spectrum signal of the first pressed soil sample without background light interference can be obtained.

For example, after the first pressed soil sample is ablated with the pulsed laser for a few microseconds to hundreds of microseconds, the atomic emission spectrum generated during the cooling and de-excitation process of the high temperature plasma with energy level transition is acquired by the spectrum acquisition device. Specifically, a delay time of the spectrum acquisition device can be 3 μs, 5 μs, 30 μs, 50 μs, 300 μs, 500 μs, or the like, and a specific delay time can be determined according to factors such as an excitation time of a laser, an acquisition time of a spectrum signal, and a trigger sequence thereof.

In another embodiment, a multi-sampling and averaging method is adopted. An ablation point of the pulsed laser output device on the surface of the first pressed soil sample is allowed to move, such that the pulsed laser output device excites the soil particles into the high temperature plasma with energy level transition at different positions on the surface of the first pressed soil sample, and the spectrum acquisition device acquires a plurality of atomic emission spectra generated during the cooling and de-excitation process of the high temperature plasma with energy level transition at different positions. Then, the acquired plurality of atomic emission spectra are subjected to baseline correction and abnormal spectrum removal to obtain the atomic emission spectrum of the first pressed soil sample. An intensity of a characteristic spectral line of carbon in the first pressed soil sample is extracted and input into the total carbon content quantification model constructed in advance to obtain the total carbon content in the soil to be tested that is output by the total carbon content quantification model.

In the present disclosure, the multi-sampling and averaging method is adopted, where the surface of the first pressed soil sample is ablated multiple times and the acquired atomic emission spectra are subjected to baseline correction and abnormal spectrum removal, so as to avoid a random error in the detection of the total carbon content in the soil to be tested and a measurement error caused by uneven samples.

The movement of the ablation point of the pulsed laser output device on the surface of the first pressed soil sample may be allowed specifically as follows: the pulsed laser output device is allowed to move horizontally, or the first pressed soil sample is allowed to move horizontally, or the first pressed soil sample is allowed to move in a horizontal direction following a sample-moving platform, but the present disclosure is not limited thereto.

Figure 7:
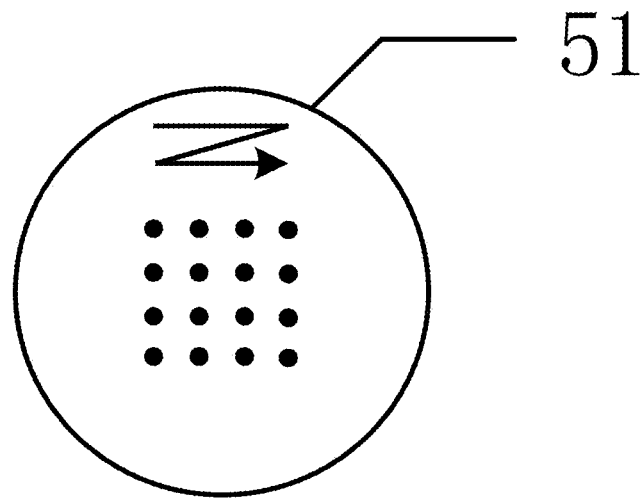
FIG. 7 is a schematic diagram of ablating a first pressed soil sample with a pulsed laser provided by the present disclosure.

FIG. 7 is a schematic diagram of ablating the first pressed soil sample with the pulsed laser provided by the present disclosure. As shown in FIG. 7, the points on the first pressed soil sample 51 are ablation points of the pulsed laser, and the arrow indicates that a direction of the pulsed laser to ablate the first pressed soil sample 51 is from left to right and from top to bottom.

With reference to the following embodiments, this step is described as follows: 1 g of a soil sample obtained after sieving and air-drying is taken to prepare a first pressed soil sample 51 that is a thin cylindrical sheet with a diameter of 10 mm, pulsed laser is output by the pulsed laser output device to ablate 16 different positions on a surface of the first pressed soil sample 51 continuously from left to right and from top to bottom, and after the first pressed soil sample is ablated with the pulsed laser for a few microseconds to hundreds of microseconds, atomic emission spectra generated during a cooling and de-excitation process of a high-temperature plasma are acquired by the spectrum acquisition device to obtain spectrum signals without background light interference of the first pressed soil sample. The acquired plurality of original atomic emission spectra are subjected to baseline correction and abnormal spectrum removal, and finally a spectral intensity of an emission spectral line corresponding to carbon is input into the total carbon content quantification model to obtain a total carbon content $C_{Total}$.

In the method for detecting soil organic matter provided by the present disclosure, soil particles are excited for transition to produce a high-temperature plasma in a high-energy state, an atomic emission spectrum generated during a cooling and de-excitation process of the high-temperature plasma is acquired, and a total carbon content in a soil can be acquired according to an intensity of a characteristic spectral line of carbon. That is, with the method of the present disclosure, a total carbon content in a soil can be acquired merely according to a relationship between an intensity of a characteristic spectral line of carbon and a content of carbon, which can allow the rapid, efficient, and accurate acquisition of a total carbon content in a soil, enhance the applicability and transplantability of the detection method, and greatly reduce the time and labor costs of detection.

Based on the above embodiments, as an optional embodiment, during a process of ablating the first pressed soil sample with the pulsed laser, an inert gas is purged around an ablation point.

The inert gas is an inert protective gas, including, but not limited to, helium, argon, or the like.

When the first pressed soil sample is ablated with the pulsed laser, the pulsed laser will also excite carbon-containing substances such as $CO_2$ in an air environment, and at this point, the inert protective gas is purged around the ablation point to prevent the contact of the carbon-containing substances such as $CO_2$ in the air environment with the first pressed soil sample and the pulsed laser, such that the pulsed laser only excites carbon in the first pressed soil sample and does not synchronously excite the carbon-containing substances such as $CO_2$ in the air, so as to obtain an atomic emission spectrum composed merely of carbon in the first pressed soil sample, which eliminates the interference of ambient gases in the air on a detection result and improves a detection accuracy. In addition, the purging of the inert gas around the ablation point can also effectively prevent the occurrence of explosion during an ablation process, and can effectively ensure the safety of personnel and objects.

Figure 8:
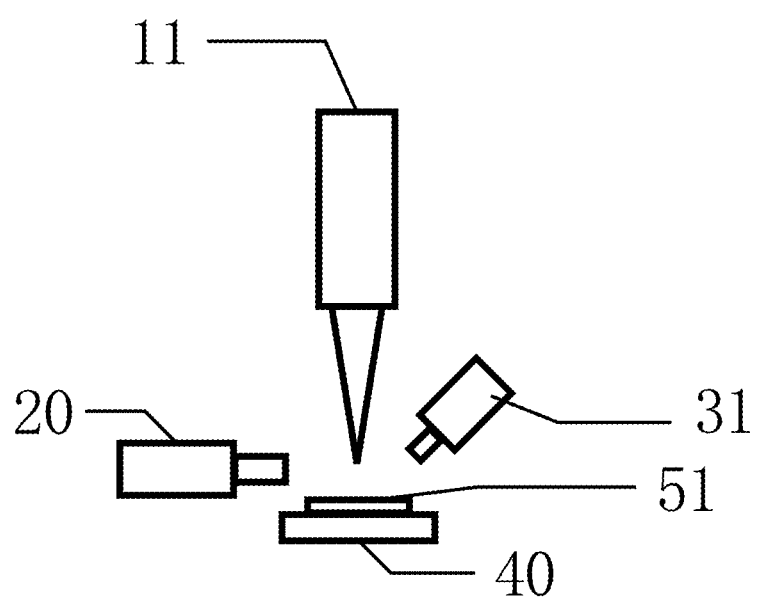
FIG. 8 is a schematic working diagram of the method for detecting a total carbon content in a soil provided by the present disclosure.

FIG. 8 is a schematic working diagram of the method for detecting a total carbon content in a soil provided by the present disclosure. As shown in FIG. 8, the pulsed laser output device 11 is arranged above the first pressed soil sample 51, the first pressed soil sample 51 is arranged above the sample-moving platform 40, a protective gas-purging device 20 is arranged at a side of a pulsed laser output position, and the spectrum acquisition device 31 is arranged above the first pressed soil sample 51 at a specified angle relative to a plane.

When the method for detecting a total carbon content in a soil provided by the present disclosure is implemented, the pulsed laser output device 11 outputs pulsed laser with a specified wavelength and energy downwards, and the pulsed laser is focused on a surface of a first pressed soil sample 51 through a focusing lens (not shown in the figures) to ablate the first pressed soil sample 51, such that soil particles in the first pressed soil sample 51 are excited into a high temperature plasma with energy level transition. During the above process, an inert protective gas is purged around an ablation point by the protective gas-purging device 20.

An atomic emission spectrum generated during a cooling and de-excitation process of the high temperature plasma with energy level transition is acquired by the spectrum acquisition device 31 and then output and displayed on an interface of the device, and the atomic emission spectrum includes characteristic spectral lines of different elements. Then, an intensity of a characteristic spectral line of carbon in the first pressed soil sample is extracted and input into the total carbon content quantification model constructed in advance to obtain the total carbon content in the soil to be tested that is output by the total carbon content quantification model.

FIG. 9 is a schematic flow chart of the method for detecting an inorganic carbon content in a soil based on diffuse reflection provided by the present disclosure. As an optional embodiment, as shown in FIG. 9, the method of the present disclosure includes, but is not limited to, the following steps:

The second pressed soil sample is irradiated with a broad-band infrared light source, and the molecular absorption spectrum of diffused light reflected by the second pressed soil sample is acquired.

A background spectrum is acquired through a blank sample, and an absorbance curve of the molecular absorption spectrum is calculated with the molecular absorption spectrum and the background spectrum.

On the absorbance curve, absorbance corresponding to a characteristic frequency band of inorganic carbon components in the soil to be tested is acquired.

The absorbance is input into a first inorganic carbon content quantification model constructed in advance to obtain the inorganic carbon content output by the first inorganic carbon content quantification model.

A wavelength of the broad-band infrared light source is in a range of 400 $cm^{-1}$ to 4,000 $cm^{-1}$.

Specifically, the present disclosure provides a method for detecting an inorganic carbon content in a soil based on diffuse reflection: The second pressed soil sample is irradiated with broad-band infrared light emitted by the broad-band infrared light source at a specified angle relative to a plane such that the broad-band infrared light is diffused by the second pressed soil sample to produce the diffused light, and the molecular absorption spectrum of the diffused light is acquired by a first infrared detection spectrometer arranged opposite to the broad-band infrared light source.

According to the molecular absorption spectrum of the second pressed soil sample and the background spectrum of the blank sample determined in advance, the absorbance curve of the molecular absorption spectrum of the second pressed soil sample is determined according to the Beer-Lambert law, the absorbance of the inorganic carbon components in the soil to be tested is acquired according to the characteristic frequency band of the inorganic carbon components in the soil to be tested on the absorbance curve and input into the first inorganic carbon content quantification model constructed in advance, and the inorganic carbon content is output by the first inorganic carbon content quantification model.

A formula for calculating the absorbance according to the Beer-Lambert law is as follows:

$$\text{Absorbance} = \log_{10} I_0 / I_1,$$

where Absorbance represents an absorbance value, $I_0$ represents an intensity of incident light, and $I_1$ represents an intensity of emergent light.

The first inorganic carbon content quantification model is a description of a relationship between the absorbance and content of inorganic carbon.

A process of constructing the first inorganic carbon content quantification model can be as follows: A plurality of samples with known inorganic carbon contents are collected, a molecular absorption spectrum of each sample is acquired by the diffuse reflectance method for acquiring a molecular absorption spectrum provided in any one of the above embodiments, and an absorbance curve of each molecular absorption spectrum is extracted. Characteristic frequency bands of inorganic carbon components in this batch of samples on absorbance curves are determined, a characteristic frequency band of absorbance of each sample is correlated with a corresponding inorganic carbon content, and these data points are fit by a regression method such as linear regression or polynomial regression to obtain the first inorganic carbon content quantification model.

The blank sample is an infrared light transmitting material sheet without a soil sample, and is prepared by the same method as the first pressed soil sample and the second pressed soil sample.

For example, the blank sample is prepared with KBr as an infrared light transmitting material as follows: 1 g of a KBr powder is taken with an electronic balance and sheeted by the sheeting tool with a fixed pressure for a fixed time to finally obtain the blank sample that has a diameter of 10 mm and is a thin cylindrical sheet.

When the background spectrum is determined in advance, a molecular absorption spectrum of the blank sample without a soil sample is acquired as the background spectrum by the diffuse reflectance method for acquiring a molecular absorption spectrum described above.

In an embodiment, the characteristic frequency band corresponding to the inorganic carbon components in the soil to be tested is an infrared waveband in a range of 1,300 $cm^{-1}$ to 1,600 $cm^{-1}$.

Figure 10:
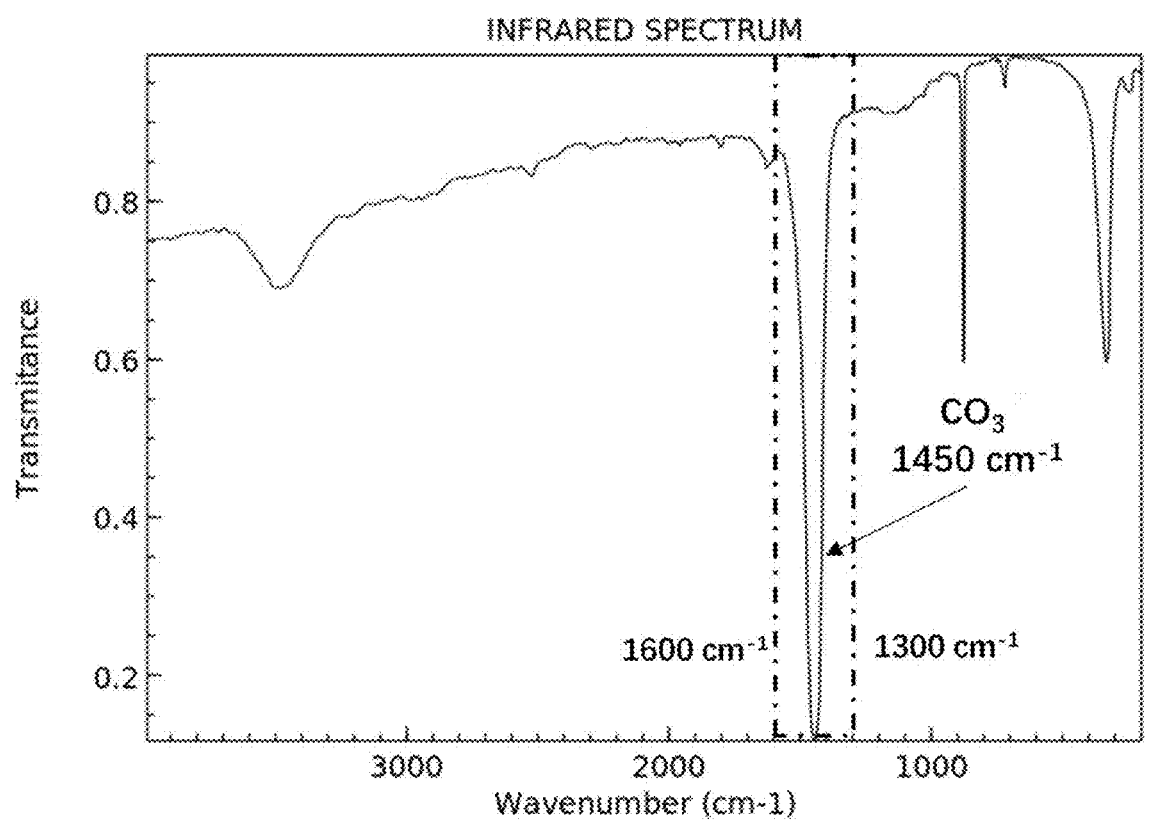
FIG. 10 is a schematic diagram of an infrared characteristic spectrum of carbonates provided by the present disclosure.

FIG. 10 is a schematic diagram of an infrared characteristic spectrum of carbonates provided by the present disclosure. As shown in FIG. 10, inorganic carbon with carbonates as a main component has significant characteristics in an infrared waveband in a range of 1,300 $cm^{-1}$ to 1,600 $cm^{-1}$ (namely, in the dashed box), and has the most significant characteristic at 1,450 $cm^{-1}$.

Figure 11:
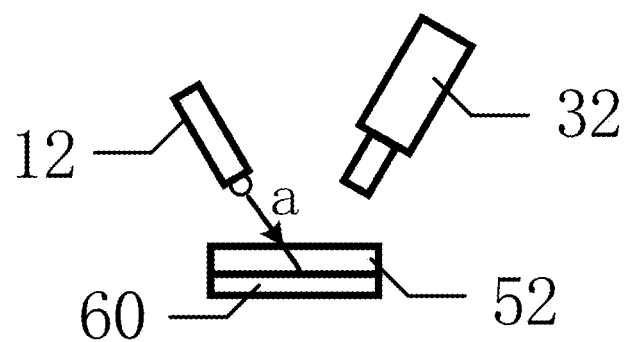
FIG. 11 is a schematic working diagram of the method for detecting an inorganic carbon content in a soil based on diffuse reflection provided by the present disclosure.

FIG. 11 is a schematic working diagram of the method for detecting an inorganic carbon content in a soil based on diffuse reflection provided by the present disclosure. As shown in FIG. 11, the second pressed soil sample 52 is placed on a sample substrate 60, the broad-band infrared light source 12 is arranged above the second pressed soil sample 52 on the left at a specified angle relative to a plane, and the first infrared detection spectrometer 32 is arranged above the second pressed soil sample 52 on the left at a specified angle relative to a plane.

When the method for detecting an inorganic carbon content in a soil based on diffuse reflection provided by the present disclosure is implemented, the broad-band infrared light source 12 emits broad-band infrared light to irradiate the second pressed soil sample 52, the broad-band infrared light is diffused by the second pressed soil sample 52 to produce diffused light, and a molecular absorption spectrum of the diffused light is acquired by the first infrared detection spectrometer 32 and then output and displayed on an interface of the device.

According to the molecular absorption spectrum of the second pressed soil sample 52 and a background spectrum of a blank sample determined in advance, an absorbance curve of the molecular absorption spectrum of the second pressed soil sample 52 is determined according to the Beer-Lambert law, and a characteristic frequency band of inorganic carbon components in the soil to be tested on the absorbance curve is determined to obtain the absorbance of the inorganic carbon components in the soil to be tested. The absorbance is input into the first inorganic carbon content quantification model constructed in advance, and the first inorganic carbon content quantification model outputs the inorganic carbon content.

In the method for detecting soil organic matter provided by the present disclosure, a molecular absorption spectrum of diffused light from a pressed soil sample is acquired, the absorbance is acquired according to a characteristic frequency band corresponding to inorganic carbon components, and an inorganic carbon content in a soil can be obtained according to the absorbance of the characteristic frequency band of inorganic carbon. That is, with the method of the present disclosure, an inorganic carbon content in a soil can be obtained merely according to a relationship between the absorbance and content, which can allow the rapid, efficient, and accurate acquisition of an inorganic carbon content in a soil, enhance the applicability and transplantability of the detection method, and greatly reduce the time and labor costs of detection.

For the detection of an inorganic carbon content in a soil, the present disclosure not only provides the diffuse reflection-based detection method in any one of the above embodiments, but also provides another parallel transmission-based detection method.

Figure 12:
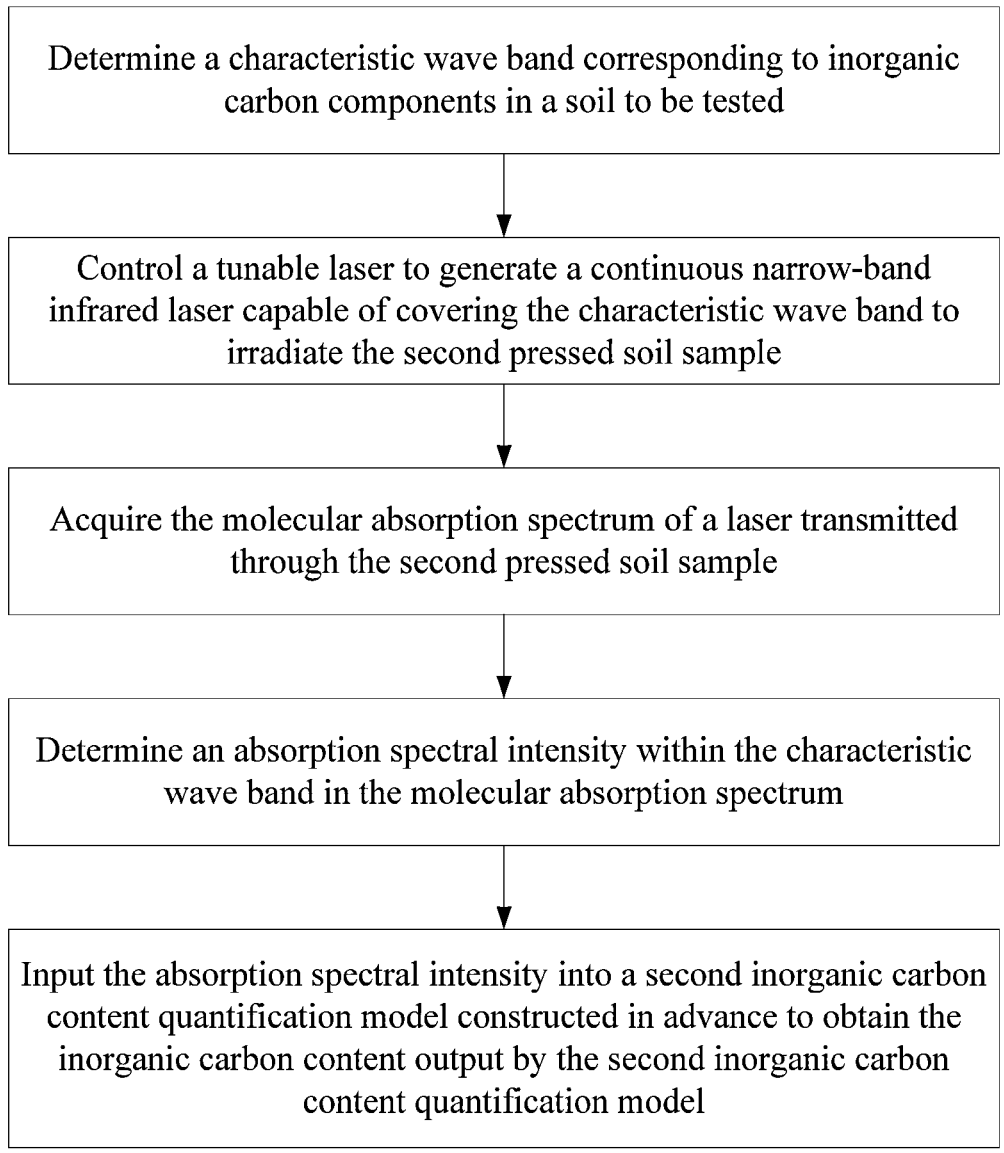
FIG. 12 is a schematic flow chart of the method for detecting an inorganic carbon content in a soil based on transmission provided by the present disclosure.

FIG. 12 is a schematic flow chart of the method for detecting an inorganic carbon content in a soil based on transmission provided by the present disclosure. As another optional embodiment, as shown in FIG. 12, the method of the present disclosure includes, but is not limited to, the following steps:

The determining the inorganic carbon content in the soil to be tested according to the molecular absorption spectrum of the second pressed soil sample specifically includes:

A characteristic waveband corresponding to inorganic carbon components in the soil to be tested is determined.

A tunable laser is controlled to generate a continuous narrow-band infrared laser capable of covering the characteristic waveband to irradiate the second pressed soil sample.

The molecular absorption spectrum of a laser transmitted through the second pressed soil sample is acquired.

An absorption spectral intensity within the characteristic waveband in the molecular absorption spectrum is determined.

The absorption spectral intensity is input into a second inorganic carbon content quantification model constructed in advance to obtain the inorganic carbon content output by the second inorganic carbon content quantification model.

The tunable laser, also known as a continuous wavelength-tunable laser, is provided with a laser controller, and the laser controller can adjust a driving current and an operating temperature of the tunable laser to adjust a wavelength of a laser output by the tunable laser. Based on this working principle, the tunable laser can output a laser of a specified wavelength band, that is, the continuous narrow-band infrared laser capable of covering the characteristic waveband corresponding to the inorganic carbon components can be produced.

Specifically, the tunable laser can be a quantum cascade laser (QCL).

Specifically, the present disclosure provides a method for detecting an inorganic carbon content in a soil based on transmission:

A continuous tunable laser capable of covering this waveband is selected according to a characteristic waveband of inorganic carbonates. Then, the tunable laser is controlled to generate the continuous narrow-band infrared laser capable of covering the above characteristic waveband to irradiate the second pressed soil sample, and the continuous narrow-band infrared laser is transmitted through the second pressed soil sample to produce the transmitted laser.

The molecular absorption spectrum of the transmitted laser is acquired by a second infrared detection spectrometer arranged opposite to the tunable laser and then output and displayed on an interface of the device, an absorption spectral intensity of the characteristic waveband corresponding to the inorganic carbon components in the soil to be tested is extracted from the molecular absorption spectrum and input into the second inorganic carbon content quantification model constructed in advance, and the second inorganic carbon content quantification model outputs the inorganic carbon content.

The second inorganic carbon content quantification model is a description of a relationship between the absorption spectral intensity and content of inorganic carbon.

A specific embodiment of constructing the second inorganic carbon content quantification model is provided below: A batch of samples with known inorganic carbon contents are collected, molecular absorption spectra of this batch of samples are acquired by the transmission method for acquiring a molecular absorption spectrum described above, and absorption spectral intensities of the characteristic waveband of inorganic carbon in the molecular absorption spectra are extracted. An absorption spectral intensity of each sample is correlated with a corresponding inorganic carbon content, and these data points are fit by a regression method such as linear regression or polynomial regression to obtain the second inorganic carbon content quantification model.

Figure 13:
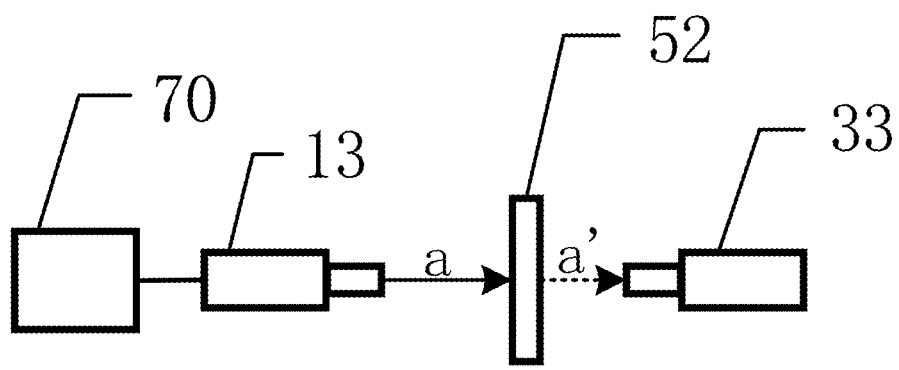
FIG. 13 is a schematic working diagram of the method for detecting an inorganic carbon content in a soil based on transmission provided by the present disclosure.

FIG. 13 is a schematic working diagram of the method for detecting an inorganic carbon content in a soil based on transmission provided by the present disclosure. As shown in FIG. 13, the second pressed soil sample 52 is arranged vertically, the tunable laser 13 is arranged just on the left of the second pressed soil sample 52, the tunable laser 13 is connected to the laser controller 70, and the second infrared detection spectrometer 33 is arranged just on the right of the second pressed soil sample 52.

When the method for detecting an inorganic carbon content in a soil based on transmission provided by the present disclosure is implemented, the tunable laser 13 produces a continuous narrow-band infrared laser capable of covering the above characteristic waveband to irradiate the second pressed soil sample 52, where the arrow a indicates an output direction of the continuous narrow-band infrared laser. The continuous narrow-band infrared laser is transmitted through the second pressed soil sample 52 to produce a transmitted laser, where the arrow a' indicates an output direction of the transmitted laser.

A molecular absorption spectrum of the transmitted laser is acquired by the second infrared detection spectrometer 33 and is output and displayed on an interface of the device, an absorption spectral intensity of the characteristic waveband corresponding to the inorganic carbon components in the soil to be tested is extracted from the molecular absorption spectrum and input into the second inorganic carbon content quantification model constructed in advance, and the second inorganic carbon content quantification model outputs the inorganic carbon content.

Compared with the diffuse reflectance spectrometry, the transmission-based molecular absorption spectrometry using a tunable laser infrared light source can allow the direct detection without relying on a background spectrum of a blank sample, and directly reflects an inorganic carbon content through a light intensity obtained by a spectrometer. Compared with the ordinary broad-band infrared light source, the continuous wavelength-tunable scanning laser has a small bandwidth and a high energy, and a spectrum signal obtained correspondingly has a strong intensity, resulting in high sensibility of detection. In addition, the laser light source has a stronger light intensity than the ordinary infrared ceramic light source due to a high power, and thus can penetrate through a thick soil sample. In other words, when the method for detecting an inorganic carbon content in a soil based on transmission provided by the present disclosure is adopted, an increased number of soil samples can participate in infrared absorption with a long optical path, which can play a signal enhancement role. In addition, the wavelength-tunable scanning laser has a small bandwidth, which eliminates the spectral interference of other components in a soil to some extent.

In summary, in the method for detecting soil organic matter provided by the present disclosure, a tunable laser and a laser transmission method are adopted to detect an inorganic carbon content in a soil, there is no need to determine a background spectrum of a blank sample, and the inorganic carbon content can be directly reflected by a spectral intensity, which reduces the operation steps. In addition, the tunable laser has a small bandwidth and a high resolution, which eliminates the spectral interference of other components in the soil to some extent.

Figure 14:
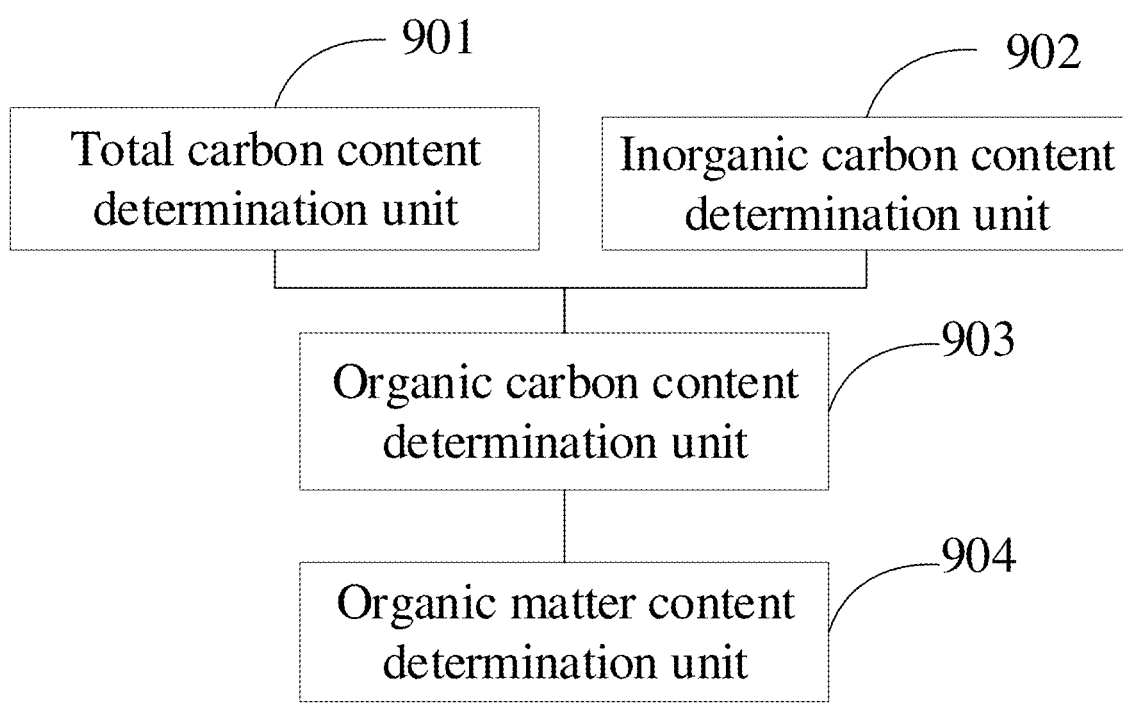
FIG. 14 is a schematic structural diagram of the device for detecting soil organic matter provided by the present disclosure.

FIG. 14 is a schematic structural diagram of the device for detecting soil organic matter provided by the present disclosure. As shown in FIG. 14, the device of the present disclosure includes, but is not limited to:

a total carbon content determination unit 901 configured to determine a total carbon content in a soil to be tested according to an atomic emission spectrum of a first pressed soil sample, where the first pressed soil sample is a sample of the soil to be tested;

an inorganic carbon content determination unit 902 configured to determine an inorganic carbon content in the soil to be tested according to a molecular absorption spectrum of a second pressed soil sample, where the second pressed soil sample is prepared by mixing the sample of the soil to be tested with an infrared light transmitting material in a preset ratio;

an organic carbon content determination unit 903 configured to determine an organic carbon content in the soil to be tested according to a difference between the total carbon content and the inorganic carbon content; and an organic matter content determination unit 904 configured to determine an organic matter content in the soil to be tested according to the organic carbon content.

It should be noted that the device for detecting soil organic matter provided by the present disclosure can implement the method for detecting soil organic matter described in any one of the above embodiments during a specific operation, which will not be described in detail in this embodiment.

In the device for detecting soil organic matter provided by the present disclosure, based on the distinct characteristics of carbon and inorganic carbon in an atomic emission spectrum and a molecular absorption spectrum, the atomic emission spectroscopy technology and the molecular absorption spectroscopy technology are used in combination. Different light sources are used to ablate or irradiate different pressed soil samples to obtain a total carbon content and an inorganic carbon content in a soil, and an organic matter content is calculated. For soils in different regions, there is no need of a large number of samples to construct an organic matter content inversion model, which improves the universality and transplantability of the detection method and reduces the time and labor costs of soil organic matter detection.

The present disclosure also provides a system for detecting soil organic matter, including, but not limited to:

a pulsed laser output device 11 configured to output pulsed laser;

a focusing lens configured to focus the pulsed laser to ablate a first pressed soil sample 51;

a protective gas-purging device 20 configured to purge an inert gas around an ablation point of the first pressed soil sample 51;

a spectrum acquisition device 31 arranged opposite to the pulsed laser output device and configured to acquire an atomic emission spectrum generated after soil particles in the first pressed soil sample 51 are excited into a high temperature plasma with energy level transition;

a sample-moving platform 40 configured to carry the first pressed soil sample 51 and adjust an ablation point of the pulsed laser by controlling the first pressed soil sample to move in different directions;

a broad-band infrared light source 12 configured to output broad-band infrared light to a second pressed soil sample 52; and a first infrared detection spectrometer 32 arranged opposite to the broad-band infrared light source and configured to acquire a molecular absorption spectrum of diffused light reflected by the second pressed soil sample 52.

The pulsed laser output device 11 includes, but is not limited to, a plasma emission spectrum detection device, a Q-switched Nd:YAG laser, or the like.

The broad-band infrared light source 12 includes, but is not limited to, a silicon carbide rod broad-band infrared light source, a ceramic rod broad-band infrared light source, or the like, but the present disclosure is not limited thereto.

The first infrared detection spectrometer 32 can be a Fourier transform infrared (FTIR) spectrometer.

It should be noted that the system for detecting soil organic matter provided by the present disclosure can implement the method for detecting soil organic matter provided by the present disclosure during a specific operation, which will not be described in detail in this embodiment.

In the system for detecting soil organic matter provided by the present disclosure, based on the distinct characteristics of carbon and inorganic carbon in an atomic emission spectrum and a molecular absorption spectrum, the atomic emission spectroscopy technology and the molecular absorption spectroscopy technology are used in combination. Different light sources are used to ablate or irradiate different pressed soil samples to obtain a total carbon content and an inorganic carbon content in a soil, and an organic matter content is calculated. For soils in different regions, there is no need of a large number of samples to construct an organic matter content inversion model, which improves the universality and transplantability of the detection method and reduces the time and labor costs of soil organic matter detection.

Based on the above embodiments, as an optional embodiment, the system for detecting soil organic matter further includes:

a tunable laser 13 provided with a laser controller 70 and configured to generate a continuous narrow-band infrared laser capable of covering a characteristic waveband corresponding to inorganic carbon components; and a second infrared detection spectrometer 33 arranged opposite to the tunable laser 13 and configured to acquire a molecular absorption spectrum of a laser transmitted through the second pressed soil sample 52.

The tunable laser includes, but is not limited to, a continuous wavelength-tunable scanning laser.

Based on the above embodiments, as an optional embodiment, the system for detecting soil organic matter further involves the following: a substrate of the second pressed soil sample 52 is a high-reflectivity substrate 62.

Generally, the substrate of the second pressed soil sample 52 is an ordinary substrate such as a glass sheet, a plastic sheet, or a polymer film. The ordinary substrate basically has no infrared light-reflecting ability, and broad-band infrared light will directly penetrate through the ordinary substrate.

Therefore, a signal received by the first infrared detection spectrometer 32 is a diffuse reflection signal of the second pressed soil sample 52, and there is no infrared spectral characteristic-enhancing effect.

However, compared with the ordinary substrate, the high-reflectivity substrate 62, as the substrate of the second pressed soil sample 52, can reflect transmitted light from broad-band infrared light incident on the second pressed soil sample 52, and the transmitted light penetrates through the second pressed soil sample 52, thereby increasing an action range and an optical path of the broad-band infrared light for the second pressed soil sample 52, namely, enhancing an infrared spectral absorption characteristic of a sample.

In some embodiments, the high-reflectivity substrate 62 is a high-purity gold-plated plate with infrared reflectivity of 0.95 or more.

Figure 15:
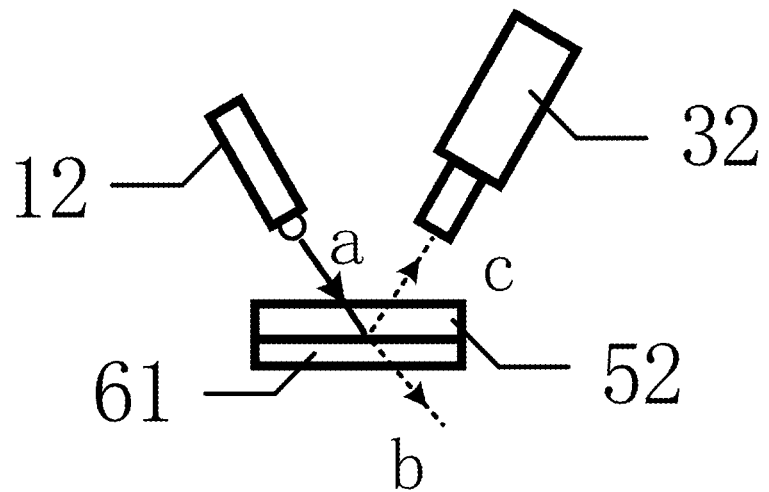
FIG. 15 is a schematic diagram of the direction of diffused light from a second pressed soil sample with an ordinary substrate provided by the present disclosure.

FIG. 15 is a schematic diagram of a direction of diffused light from the second pressed soil sample with an ordinary substrate provided by the present disclosure. As shown in FIG. 15, a indicates broad-band infrared light and a direction thereof, b indicates transmitted light produced after broad-band infrared light penetrates through the ordinary substrate 61 and a direction thereof, and c indicates diffused light produced after broad-band infrared light irradiates the second pressed soil sample 52 and a direction thereof.

Figure 16:
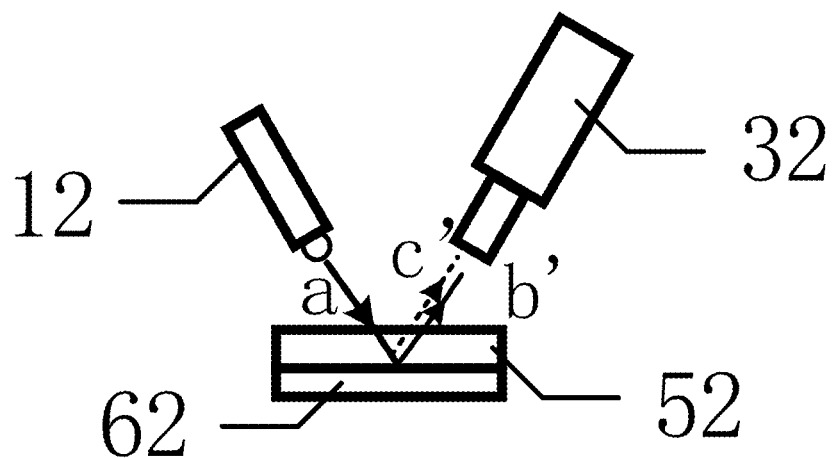
FIG. 16 is a schematic diagram of the direction of diffused light from a second pressed soil sample with a high-reflectivity substrate provided by the present disclosure.

FIG. 16 is a schematic diagram of a direction of diffused light from the second pressed soil sample with a high-reflectivity substrate provided by the present disclosure. As shown in FIG. 16, a' indicates broad-band infrared light and a direction thereof, b' indicates reflected light produced after broad-band infrared light penetrates through the second pressed soil sample 52, then is reflected by the high-reflectivity substrate 62, and then penetrates through the second pressed soil sample 52 and a direction thereof, and c' indicates diffused light produced after broad-band infrared light irradiates the second pressed soil sample 52 and a direction thereof.

As shown in FIG. 15 and FIG. 16, when the high-reflectivity substrate 62 is adopted as the substrate of the second pressed soil sample 52, broad-band infrared light can penetrate through the second pressed soil sample 52 twice, which increases an action range and an optical path of the broad-band infrared light for the second pressed soil sample 52 and enhances a molecular absorption spectral characteristic of the second pressed soil sample 52.

In the system for detecting soil organic matter provided by the present disclosure, the high-reflectivity substrate can reflect broad-band infrared light penetrating through the second pressed soil sample, and thus the broad-band infrared light can penetrate through the second pressed soil sample twice, such that a molecular absorption spectrum of the second pressed soil sample has clear characteristics, which improves the sensitivity of detection of an inorganic carbon content and an organic matter content in a soil.

Finally, in order to well illustrate a work flow of the method, device, and system for detecting soil organic matter provided by the present disclosure, a specific embodiment is provided for detailed description.

Figure 17:
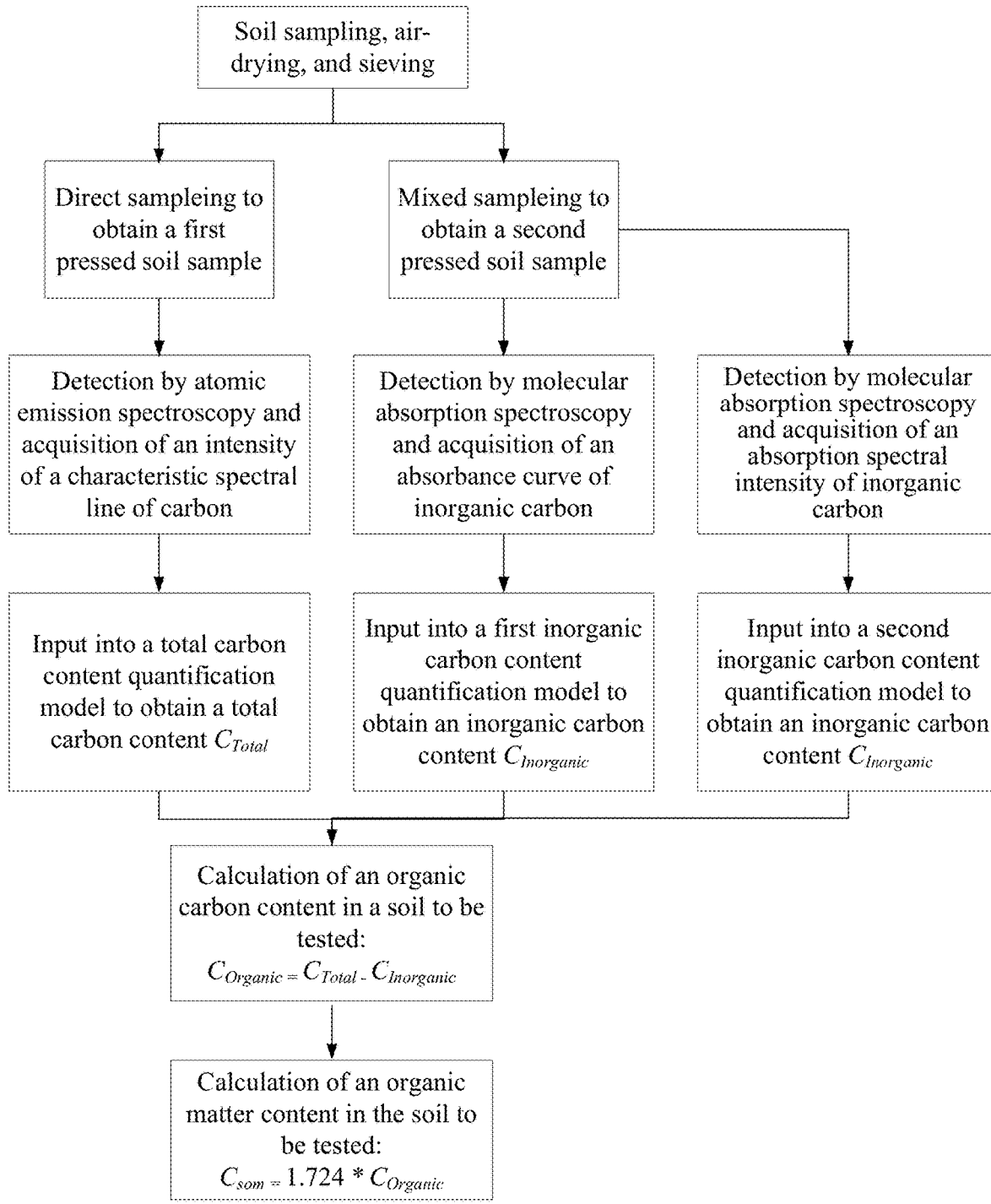
FIG. 17 is a complete work flow diagram of the method for detecting soil organic matter provided by the present disclosure.

FIG. 17 is a complete work flow diagram of the method for detecting soil organic matter provided by the present disclosure. As shown in FIG. 17, the detection of soil organic matter mainly includes the following steps: preparation of pressed soil samples, detection of a total carbon content, detection of an inorganic carbon content, determination of an organic carbon content, and determination of an organic matter content.

Preparation of pressed soil samples: An original soil sample is extracted at a designated site, sieved through an 8-mesh sieve to remove impurities such as large particles, gravel, and deciduous grass roots, naturally air-dried to reduce the moisture, and then sieved through a 60-mesh sieve to obtain a soil powder with uniform small particles.

2 g of the soil powder with uniform small particles is taken with a weighing balance and sheeted by an automatic sheeting machine to prepare a first pressed soil sample that has a diameter of 10 mm and is a thin cylindrical sheet. The first pressed soil sample is provided to detect a total carbon content in a soil.

0.04 g of the soil powder with uniform small particles and 2 g of a KBr powder were taken with a weighing balance, thoroughly mixed, and sheeted by an automatic sheeting machine to prepare a second pressed soil sample that has a diameter of 10 mm and is a thin cylindrical sheet. The second pressed soil sample is provided to detect an inorganic carbon content in a soil.

Detection of a total carbon content: The first pressed soil sample is placed on the sample-moving platform of a total carbon content detection device. A Q-switched Nd:YAG laser is adopted as the pulsed laser output device, and an emission wavelength of a pulsed laser is 1,064 nm. The laser is adjusted to make a pulsed laser beam focused on a surface of the first pressed soil sample for ablation, such that soil particles in the first pressed soil sample are excited into a high temperature plasma with energy level transition. The acquisition optical fiber of the spectrum acquisition device is arranged above the sample-moving platform to acquire an optical signal generated during a cooling and de-excitation process of the high temperature plasma with energy level transition at an angle of 45° relative to a horizontal direction, thereby producing an atomic emission spectrum.

When the laser emits the pulsed laser to ablate a soil sample, a protective gas is purged around an ablation site to clear ambient gases around the ablation site, which can ensure that an atomic emission spectrum produced after laser ablation is generated by the first pressed soil sample, and prevent the occurrence of explosion to some extent.

When an atomic emission spectrum is acquired by the spectrum acquisition device, an excitation time of the laser, a purge time of the purge gas, an acquisition time of the spectrum signal, and a trigger sequence thereof are also recorded.

An intensity of a characteristic spectral line of carbon at 247.8 nm on the atomic emission spectrum is extracted by an analysis component of the spectrum acquisition device and input into a total carbon content quantification model to calculate a total carbon content $C_{Total}$ corresponding to the soil to be tested.

The present disclosure also provides a method for detecting an inorganic carbon content, which can adopt any one of the following three modes:

1. Ordinary diffuse reflection-based detection mode: The second pressed soil sample is placed on the ordinary substrate and irradiated with broad-band infrared light emitted by the broad-band infrared light source at a specified angle relative to a plane, and a molecular absorption spectrum of diffused light produced after the broad-band infrared light penetrates through the second pressed soil sample is acquired by the first infrared detection spectrometer arranged opposite to the broad-band infrared light source at a specified angle.

After the molecular absorption spectrum of diffused light is acquired, an absorbance value in an infrared waveband in a range of 1,300 $cm^{-1}$ to 1,600 $cm^{-1}$ on the molecular absorption spectrum of diffused light is extracted and input into the first inorganic carbon content quantification model constructed in advance based on the absorbance of the corresponding waveband obtained in the previous step, so as to obtain an inorganic carbon content $C_{Inorganic}$ in the second pressed soil sample.

2. Enhanced diffuse reflection-based detection mode: The enhanced diffuse reflection-based detection mode is the same as the above-mentioned ordinary diffuse reflection-based detection mode except that the second pressed soil sample is placed on a high-reflectivity substrate.

3. Transmission-based detection mode: Inorganic carbon components in a soil to be tested are determined, and a characteristic waveband corresponding to the inorganic carbon components in the soil to be tested is determined. During actual detection, the tunable laser only emits a continuous narrow-band infrared laser corresponding to the characteristic waveband to irradiate the second pressed soil sample.

A molecular absorption spectrum of a laser transmitted through the second pressed soil sample is acquired by the second infrared detection spectrometer, an absorption spectral intensity of the characteristic waveband corresponding to the inorganic carbon components in the soil to be tested is extracted from the molecular absorption spectrum and input into the second inorganic carbon content quantification model constructed in advance, and the second inorganic carbon content quantification model outputs an inorganic carbon content $C_{Inorganic}$.

The inorganic carbon content $C_{Inorganic}$ is subtracted from the total carbon content $C_{Total}$ detected above to determine an organic carbon content $C_{Organic}$ in the soil to be tested, and finally the organic carbon content $C_{Organic}$ is multiplied by a coefficient of 1.724 to obtain an organic matter content $C_{som}$ in the soil to be tested.

The device embodiments described above are merely schematic, where the unit described as a separate component may or may not be physically separated, and a component displayed as a unit may or may not be a physical unit, that is, the component may be located at one place, or distributed on a plurality of network units. Some or all of the modules may be selected based on actual needs to allow the objectives of the solutions of the embodiments. A person of ordinary skill in the art can understand and implement the embodiments without creative efforts.

Through the description of the foregoing implementations, a person skilled in the art can clearly understand that the implementations can be implemented by means of software plus a necessary universal hardware platform, or certainly, can be implemented by hardware. Based on such understanding, the technical solutions essentially or the part contributing to the prior art may be implemented in a form of a software product. The computer software product may be stored in a computer-readable storage medium such as a ROM/RAM, a magnetic disk, or an optical disk, and includes several instructions for enabling a computer device (which may be a personal computer, a server, a network device, or the like) to execute the method according to each of the embodiments or parts of the embodiments.

Finally, it should be noted that the above embodiments are only used to illustrate the technical solutions of the present disclosure, and are not intended to limit the present disclosure. Although the present disclosure is described in detail with reference to the foregoing embodiments, a person of ordinary skill in the art should understand that he/she can still modify the technical solutions described in the foregoing embodiments, or make equivalent substitutions to some technical features therein. These modifications or substitutions do not make the essence of the corresponding technical solutions depart from the spirit and scope of the technical solutions in the embodiments of the present disclosure.

What is claimed:

1. A method for detecting soil organic matter, comprising:
   determining a total carbon content in a soil to be tested according to an atomic emission spectrum of a first pressed soil sample, wherein the first pressed soil sample is a sample of the soil to be tested;
   determining an inorganic carbon content in the soil to be tested according to a molecular absorption spectrum of a second pressed soil sample, wherein the second pressed soil sample is prepared by mixing the sample of the soil to be tested with an infrared light transmitting material in a preset ratio, wherein the inorganic carbon content is a content of carbonates in the soil to be tested;
   determining an organic carbon content in the soil to be tested according to a difference between the total carbon content and the inorganic carbon content; and
   determining an organic matter content in the soil to be tested according to the organic carbon content;
   wherein the determining a total carbon content in a soil to be tested according to an atomic emission spectrum of a first pressed soil sample specifically comprises:
   ablating the first pressed soil sample with pulsed laser to excite soil particles in the first pressed soil sample into a high temperature plasma with energy level transition;
   acquiring the atomic emission spectrum generated during a cooling and de-excitation process of the high temperature plasma with energy level transition;
   extracting an intensity of a characteristic spectral line of carbon from the atomic emission spectrum; and
   inputting the intensity of the characteristic spectral line of the carbon into a total carbon content quantification model constructed in advance to obtain the total carbon content output by the total carbon content quantification model; and
   the determining an inorganic carbon content in the soil to be tested according to a molecular absorption spectrum of a second pressed soil sample specifically comprises:
   irradiating the second pressed soil sample with a broad-band infrared light source, and acquiring the molecular absorption spectrum of diffused light reflected by the second pressed soil sample;
   acquiring a background spectrum through a blank sample, and calculating an absorbance curve of the molecular absorption spectrum with the molecular absorption spectrum and the background spectrum;
   on the absorbance curve, acquiring absorbance corresponding to a characteristic frequency band of inorganic carbon components in the soil to be tested; and
   inputting the absorbance into a first inorganic carbon content quantification model constructed in advance to obtain the inorganic carbon content output by the first inorganic carbon content quantification model.

2. The method for detecting soil organic matter according to claim 1, wherein during a process of ablating the first pressed soil sample with the pulsed laser, an inert gas is purged around an ablation point.

3. The method for detecting soil organic matter according to claim 1, wherein a wavelength of the broad-band infrared light source is in a range of 400 $cm^{-1}$ to 4,000 $cm^{-1}$.

4. The method for detecting soil organic matter according to claim 1, wherein the determining an inorganic carbon content in the soil to be tested according to a molecular absorption spectrum of a second pressed soil sample specifically comprises:
 determining a characteristic waveband corresponding to inorganic carbon components in the soil to be tested;
 controlling a tunable laser to generate a continuous narrow-band infrared laser capable of covering the characteristic waveband to irradiate the second pressed soil sample;
 acquiring the molecular absorption spectrum of a laser transmitted through the second pressed soil sample;
 determining an absorption spectral intensity within the characteristic waveband in the molecular absorption spectrum; and
 inputting the absorption spectral intensity into a second inorganic carbon content quantification model constructed in advance to obtain the inorganic carbon content output by the second inorganic carbon content quantification model.

5. The method for detecting soil organic matter according to claim 4, wherein the characteristic waveband is in a range of 1,300 $cm^{-1}$ to 1,600 $cm^{-1}$.

6. The method for detecting soil organic matter according to claim 1, wherein the determining an organic matter content in the soil to be tested according to the organic carbon content comprises:
 inputting the organic carbon content into an organic matter content quantification model constructed in advance to obtain the organic matter content output by the organic matter content quantification model.

7. A device for detecting soil organic matter, comprising:
 a total carbon content determination unit configured to determine a total carbon content in a soil to be tested according to an atomic emission spectrum of a first pressed soil sample, wherein the first pressed soil sample is a sample of the soil to be tested;
 an inorganic carbon content determination unit configured to determine an inorganic carbon content in the soil to be tested according to a molecular absorption spectrum of a second pressed soil sample, wherein the second pressed soil sample is prepared by mixing the sample of the soil to be tested with an infrared light transmitting material in a preset ratio, wherein the inorganic carbon content is a content of carbonates in the soil to be tested;
 an organic carbon content determination unit configured to determine an organic carbon content in the soil to be tested according to a difference between the total carbon content and the inorganic carbon content; and
 an organic matter content determination unit configured to determine an organic matter content in the soil to be tested according to the organic carbon content;
 wherein the total carbon content determination unit is further configured to:
  ablate the first pressed soil sample with pulsed laser to excite soil particles in the first pressed soil sample into a high temperature plasma with energy level transition;
  acquire the atomic emission spectrum generated during a cooling and de-excitation process of the high temperature plasma with energy level transition;
  extract an intensity of a characteristic spectral line of carbon from the atomic emission spectrum; and
  input the intensity of the characteristic spectral line of the carbon into a total carbon content quantification model constructed in advance to obtain the total carbon content output by the total carbon content quantification model;
 and wherein the inorganic carbon content determination unit is further configured to:
  irradiate the second pressed soil sample with a broad-band infrared light source, and acquire the molecular absorption spectrum of diffused light reflected by the second pressed soil sample;
  acquire a background spectrum through a blank sample, and calculate an absorbance curve of the molecular absorption spectrum with the molecular absorption spectrum and the background spectrum;
  on the absorbance curve, acquire absorbance corresponding to a characteristic frequency band of inorganic carbon components in the soil to be tested; and
  input the absorbance into a first inorganic carbon content quantification model constructed in advance to obtain the inorganic carbon content output by the first inorganic carbon content quantification model.

8. A system for detecting soil organic matter, at least comprising the device for detecting soil organic matter according to claim 7 and further comprising:
 a pulsed laser output device configured to output pulsed laser;
 a focusing lens configured to focus the pulsed laser to ablate the first pressed soil sample;
 a protective gas-purging device configured to purge an inert gas around an ablation point of the first pressed soil sample;
 a spectrum acquisition device arranged opposite to the pulsed laser output device and configured to acquire the atomic emission spectrum generated after soil particles in the first pressed soil sample are excited into a high temperature plasma with energy level transition;
 a sample-moving platform configured to carry the first pressed soil sample and adjust an ablation point of the pulsed laser by controlling the first pressed soil sample to move in different directions;
 a broad-band infrared light source configured to output broad-band infrared light to the second pressed soil sample; and
 a first infrared detection spectrometer arranged opposite to the broad-band infrared light source and configured to acquire the molecular absorption spectrum of diffused light reflected by the second pressed soil sample.

9. The system for detecting soil organic matter according to claim 8, further comprising:
 a tunable laser provided with a laser controller and configured to generate a continuous narrow-band infrared laser capable of covering a characteristic waveband corresponding to inorganic carbon components; and
 a second infrared detection spectrometer arranged opposite to the tunable laser and configured to acquire the molecular absorption spectrum of a laser transmitted through the second pressed soil sample.

10. The system for detecting soil organic matter according to claim 8, wherein a substrate of the second pressed soil sample is a high-reflectivity substrate.

* * * * *